(12) United States Patent
Miller et al.

(10) Patent No.: US 7,968,721 B2
(45) Date of Patent: *Jun. 28, 2011

(54) LARGE-SCALE SYNTHESIS OF SELECTIVE ANDROGEN RECEPTOR MODULATORS

(75) Inventors: Duane D. Miller, Germantown, TN (US); Karen A. Veverka, Cordova, TN (US); Kiwon Chung, Collierville, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 1179 days.

This patent is subject to a terminal disclaimer.

(21) Appl. No.: 10/754,626

(22) Filed: Jan. 12, 2004

(65) Prior Publication Data

US 2004/0260092 A1    Dec. 23, 2004

Related U.S. Application Data

(60) Provisional application No. 60/439,416, filed on Jan. 13, 2003.

(51) Int. Cl.
C07D 215/00 (2006.01)
C07D 209/04 (2006.01)
C07C 205/00 (2006.01)
C07C 391/00 (2006.01)
C07C 311/00 (2006.01)
C07C 233/00 (2006.01)
C07C 235/00 (2006.01)

(52) U.S. Cl. .......... 546/153; 548/491; 560/20; 562/899; 564/90; 564/161; 564/164

(58) Field of Classification Search ............ 546/153; 548/491; 562/899; 560/20; 564/90, 161, 564/162, 163, 164
See application file for complete search history.

(56) References Cited

U.S. PATENT DOCUMENTS

| | | | | |
|---|---|---|---|---|
| 4,636,505 A * | 1/1987 | Tucker | | 514/256 |
| 6,071,957 A | 6/2000 | Miller et al. | | |
| 6,160,011 A | 12/2000 | Miller et al. | | |
| 6,482,861 B2 | 11/2002 | Miller et al. | | |
| 6,492,554 B2 * | 12/2002 | Dalton et al. | | 564/158 |
| 6,569,896 B2 * | 5/2003 | Dalton et al. | | 514/493 |
| 6,995,284 B2 * | 2/2006 | Dalton et al. | | 564/155 |
| 7,205,437 B2 * | 4/2007 | Dalton et al. | | 564/158 |
| 7,518,013 B2 * | 4/2009 | Dalton et al. | | 558/414 |
| 2004/0014975 A1 * | 1/2004 | Dalton et al. | | 546/157 |
| 2006/0009529 A1 * | 1/2006 | Dalton et al. | | 514/620 |
| 2006/0276540 A1 * | 12/2006 | Dalton et al. | | 514/521 |

FOREIGN PATENT DOCUMENTS

| | | |
|---|---|---|
| EP | 198352 | 10/1986 |
| JP | 52128329 | 4/1996 |
| WO | WO 98/58326 | 12/1998 |
| WO | WO 03/074471 | 9/2003 |

OTHER PUBLICATIONS

Ault, Addison, Techniques and Experiments for Organic Chemistry, Fifth Edition, Cornell College, Prospect Heights, Illinois.*
West, Anthony R., Solid State Chemistry and its Applications, Wiley, New York, 1988, pp. 358 & 365.*
Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
"Bioisosterism: A Rational Approach in Drug Design", Chem. Rev. 1996, 3147-3176, Patani et. al.*
Pure and Applied Chemistry, 1971, vol. 25, Issue 4, Separation in Organic Chemistry, Robert A. Chalmers, pp. 687-693.*
Patani et. al., "Bioisosterism: A Rational Approach in Drug Design", Chem. Rev., 96, 1995, pp. 3147-3176.*
Noyes, William, A, A Textbook of Organic Chemistry, 2nd Revision, Revised, 1903, pp. 1-531.*
U.S. Appl. No. 10/277,108, filed Dec. 23, 2004, Miller, et al.
Kirkovsky et al (*J. Med Chem* (2000), 43, 581-590).
Langer, Science 249:1527-1533 (1990).
Matsumoto, Endocrinol. Met. Clin. N. Am. 23:857-75 (1994).
Steinberger et al., Effect of Chronic Administration of Testosterone Enanthate on Sperm Production and Plasma Testosterone, Follicle Stimulating Hormone, and Luteinizing Hormone Levels: A Preliminary Evaluation of a Possible Male Contraceptive, Fertility and Sterility 28:1320-28 (1977).
Sundaram et al., "7 Alpha-Methyl-Nortestosterone(MENT): The Optimal Androgen for Male Contraception," Ann. Med., 25:199-205 (1993).
Tucker et al (*J. Med Chem* (1988), 31, 885-887.

(Continued)

*Primary Examiner* — Janet L Andres
*Assistant Examiner* — Heidi Reese
(74) *Attorney, Agent, or Firm* — Mark S. Cohen; Pearl Cohen Zedek Latzer, LLP

(57) ABSTRACT

This invention relates to a process for preparing a selective androgen receptor modulator (SARM) compound represented by the structure of formula I:

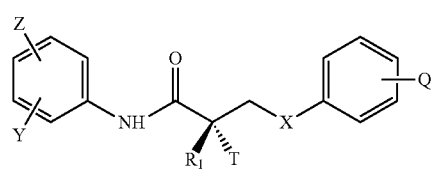

wherein X is O; and T, Z, Y, Q, R and $R_1$ are defined herein. The process includes coupling between an amide of formula II and a phenol of formula III

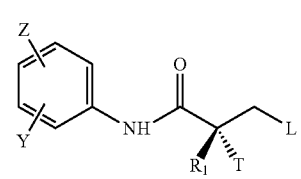

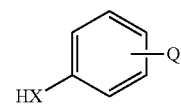

followed by a purification step consisting of precipitating the compound of formula (I) in a mixture of alcohol and water alone.

69 Claims, No Drawings

OTHER PUBLICATIONS

World Health Organization Task Force on Methods and Regulation of Male Fertility, "Contraceptive Efficacy of Testosterone-Induced Azoospermia and Oligospermia in Normal Men," Fertility and Sterility 65:821-29 (1996).

Wu, "Effects of Testosterone Enanthate in Normal Men: Experience From a Multicenter Contraceptive Efficacy Study," Fertility and Sterility 65:626-36 (1996).

Zhou, et al., Molec. Endocrinol. 9:208-18 (1995).

Buchwald et al., Surgery 88:507 (1980).

Saudek et al., N. Engl. J. Med. 321:574 (1989).

Terashima and co-workers (*Tet.* 1979, 35, 2337 ; and *Tet.* 1979, 35, 2345).

Office Action of Taiwanese Application No. 093100824 dated Aug. 6, 2008.

Office Action of Taiwanese Application No. 093100824 dated Jun. 11, 2009.

* cited by examiner

LARGE-SCALE SYNTHESIS OF SELECTIVE ANDROGEN RECEPTOR MODULATORS

CROSS REFERENCE TO RELATED APPLICATIONS

This application claims the benefit of U.S. Provisional Application Ser. No. 60/439,416, filed Jan. 13, 2003, which is incorporated in its entirety by reference herein.

GOVERNMENT INTEREST STATEMENT

This invention was made in whole or in part with government support under grant number R29 CA068096 awarded by the National Cancer Institute, National Institute of Health, and under grant number R15 HD35329, awarded by the National Institute of Child Health and Human Development, National Institute of Health. The government may have certain rights in the invention.

FIELD OF INVENTION

The present invention relates to a synthetic process for the preparation of a novel class of androgen receptor targeting agents (ARTA), which demonstrate androgenic and anabolic activity of a nonsteroidal ligand for the androgen receptor. The agents define a new subclass of compounds, which are selective androgen receptor modulators (SARMs) useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia, osteoporosis, and alterations in mood and cognition; c) treatment of conditions associated with Androgen Decline in Female (ADIF), such as sexual dysfunction, decreased sexual libido, hypogonadism, sarcopenia, osteopenia, osteoporosis, alterations in cognition and mood, depression, anemia, hair loss, obesity and endometriosis, d) treatment and/or prevention of chronic muscular wasting; e) decreasing the incidence of, halting or causing a regression of prostate cancer; f) oral androgen replacement; g) preventing and/or treating dry eye conditions; h) treatment and/or prevention of benign prostate hyperplasia (BPH); i) inducing apoptosis in a cancer cell; j) treatment and/or prevention of cancers of female sexual organs such as breast cancer, uterine cancer and ovarian cancer; and/or other clinical therapeutic and/or diagnostic areas.

BACKGROUND OF THE INVENTION

The androgen receptor ("AR") is a ligand-activated transcriptional regulatory protein that mediates induction of male sexual development and function through its activity with endogenous androgens. Androgens are generally known as the male sex hormones. The androgenic hormones are steroids, which are produced in the body by the testes and the cortex of the adrenal gland or can be synthesized in the laboratory. Androgenic steroids play an important role in many physiologic processes, including the development and maintenance of male sexual characteristics such as muscle and bone mass, prostate growth, spermatogenesis, and the male hair pattern (Matsumoto, Endocrinol. Met. Clin. N. Am. 23:857-75 (1994)). The endogenous steroidal androgens include testosterone and dihydrotestosterone ("DHT"). Testosterone is the principal steroid secreted by the testes and is the primary circulating androgen found in the plasma of males. Testosterone is converted to DHT by the enzyme 5 alpha-reductase in many peripheral tissues. DHT is thus thought to serve as the intracellular mediator for most androgen actions (Zhou, et al., Molec. Endocrinol. 9:208-18 (1995)). Other steroidal androgens include esters of testosterone, such as the cypionate, propionate, phenylpropionate, cyclopentylpropionate, isocarporate, enanthate, and decanoate esters, and other synthetic androgens such as 7-Methyl-Nortestosterone ("MENT") and its acetate ester (Sundaram et al., "7 Alpha-Methyl-Nortestosterone(MENT): The Optimal Androgen For Male Contraception," Ann. Med., 25:199-205 (1993) ("Sundaram")). Because the AR is involved in male sexual development and function, the AR is a likely target for effecting male contraception or other forms of hormone replacement therapy.

Worldwide population growth and social awareness of family planning have stimulated a great deal of research in contraception. Contraception is a difficult subject under any circumstance. It is fraught with cultural and social stigma, religious implications, and, most certainly, significant health concerns. This situation is only exacerbated when the subject focuses on male contraception. Despite the availability of suitable contraceptive devices, historically, society has looked to women to be responsible for contraceptive decisions and their consequences. Although concern over sexually transmitted diseases has made men more aware of the need to develop safe and responsible sexual habits, women still often bear the brunt of contraceptive choice. Women have a number of choices, from temporary mechanical devices such as sponges and diaphragms to temporary chemical devices such as spermicides. Women also have at their disposal more permanent options, such as physical devices including IUDs and cervical caps as well as more permanent chemical treatments such as birth control pills and subcutaneous implants. However, to date, the only options available for men include the use of condoms and vasectomy. Condom use, however is not favored by many men because of the reduced sexual sensitivity, the interruption in sexual spontaneity, and the significant possibility of pregnancy caused by breakage or misuse. Vasectomies are also not favored. If more convenient methods of birth control were available to men, particularly long-term methods which require no preparative activity immediately prior to a sexual act, such methods could significantly increase the likelihood that men would take more responsibility for contraception.

Administration of the male sex steroids (e.g., testosterone and its derivatives) has shown particular promise in this regard due to the combined gonadotropin-suppressing and androgen-substituting properties of these compounds (Steinberger et al., "Effect of Chronic Administration of Testosterone Enanthate on Sperm Production and Plasma Testosterone, Follicle Stimulating Hormone, and Luteinizing Hormone Levels: A Preliminary Evaluation of a Possible Male Contraceptive, Fertility and Sterility 28:1320-28 (1977)). Chronic administration of high doses of testosterone completely abolishes sperm production (azoospermia) or reduces it to a very low level (oligospermia). The degree of spermatogenic suppression necessary to produce infertility is not precisely known. However, a recent report by the World Health Organization showed that weekly intramuscular injections of testosterone enanthate result in azoospermia or severe oligospermia (i.e., less than 3 million sperm per ml) and infertility in 98% of men receiving therapy (World Health Organization Task Force on Methods And Regulation of Male Fertility, "Contraceptive Efficacy of Testosterone-Induced Azoospermia and Oligospermia in Normal Men," Fertility and Sterility 65:821-29 (1996)).

A variety of testosterone esters have been developed which are more slowly absorbed after intramuscular injection and thus result in greater androgenic effect. Testosterone enanthate is the most widely used of these esters. While testosterone enanthate has been valuable in terms of establishing the feasibility of hormonal agents for male contraception, it has several drawbacks, including the need for weekly injections and the presence of supraphysiologic peak levels of testosterone immediately following intramuscular injection (Wu, "Effects of Testosterone Enanthate in Normal Men: Experience From a Multicenter Contraceptive Efficacy Study," Fertility and Sterility 65:626-36 (1996)).

Steroidal ligands which bind the AR and act as androgens (e.g. testosterone enanthate) or as antiandrogens (e.g. cyproterone acetate) have been known for many years and are used clinically (Wu 1988). Although nonsteroidal antiandrogens are in clinical use for hormone-dependent prostate cancer, nonsteroidal androgens have not been reported. For this reason, research on androgens useful for male contraception and hormone replacement has focused solely on steroidal compounds.

Prostate cancer is one of the most frequently occurring cancers among men in the United States, with hundreds of thousands of new cases diagnosed each year. Unfortunately, over sixty percent of newly diagnosed cases of prostate cancer are found to be pathologically advanced, with no cure and a dismal prognosis. One approach to this problem is to find prostate cancer earlier through screening programs and thereby reduce the number of advanced prostate cancer patients. Another strategy, however, is to develop drugs to prevent prostate cancer. One third of all men over 50 years of age have a latent form of prostate cancer that may be activated into the life-threatening clinical prostate cancer form. The frequency of latent prostatic tumors has been shown to increase substantially with each decade of life from the 50s (5.3-14%) to the 90s (40-80%). The number of people with latent prostate cancer is the same across all cultures, ethnic groups, and races, yet the frequency of clinically aggressive cancer is markedly different. This suggests that environmental factors may play a role in activating latent prostate cancer. Thus, the development of treatment and preventative strategies against prostate cancer may have the greatest overall impact both medically and economically against prostate cancer.

"BPH (benign prostate hyperplasia)" is a nonmalignant enlargement of the prostate gland, and is the most common non-malignant proliferative abnormality found in any internal organ and the major cause of morbidity in the adult male. BPH occurs in over 75% of men over 50 years of age, reaching 88% prevalence by the ninth decade. BPH frequently results in a gradual squeezing of the portion of the urethra which traverses the prostate (prostatic urethra). This causes patients to experience a frequent urge to urinate because of incomplete emptying of the bladder and urgency of urination. The obstruction of urinary flow can also lead to a general lack of control over urination, including difficulty initiating urination when desired, as well as difficulty in preventing urinary flow because of the inability to empty urine from the bladder, a condition known as overflow urinary incontinence, which can lead to urinary obstruction and to urinary failure.

Osteoporosis is a systemic skeletal disease, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5-20% of patients dying within one year, and over 50% of survivors being incapacitated. The elderly are at greatest risk of osteoporosis, and the problem is therefore predicted to increase significantly with the aging of the population. Worldwide fracture incidence is forecasted to increase three-fold over the next 60 years, and one study estimated that there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle and low calcium intake. However, osteoporosis also occurs frequently in males. It is well established that the bone mineral density of males decrease with age. Decreased amounts of bone mineral content and density correlates with decreased bone strength, and predisposes to fracture. The molecular mechanisms underlying the pleiotropic effects of sex hormones in non-reproductive tissues are only beginning to be understood, but it is clear that physiologic concentrations of androgens and estrogens play an important role in maintaining bone homeostasis throughout the life cycle. Consequently, when androgen or estrogen deprivation occurs there is a resultant increase in the rate of bone remodeling that tilts the balance of resorption and formation to the favor of resorption that contributes to the overall loss of bone mass. In males, the natural decline in sex hormones at maturity (direct decline in androgens as well as lower levels of estrogens derived from peripheral aromatization of androgens) is associated with the frailty of bones. This effect is also observed in males who have been castrated.

Androgen decline in the aging male (ADAM) refers to a progressive decrease in androgen production, common in males after middle age. The syndrome is characterized by alterations in the physical and intellectual domains that correlate with and can be corrected by manipulation of the androgen milieu. ADAM is characterized biochemically by a decrease not only in serum androgen, but also in other hormones, such as growth hormone, melatonin and dehydroepiandrosterone. Clinical manifestations include fatigue, depression, decreased libido, sexual dysfunction, erectile dysfunction, hypogonadism, osteoporosis, hair loss, obesity, sarcopenia, osteopenia, anemia, and alterations in mood and cognition.

Androgen Deficiency in Female (ADIF) refers to a variety of hormone-related conditions including, common in females after middle age. The syndrome is characterized by sexual dysfunction, decreased sexual libido, hypogonadism, sarcopenia, osteopenia, osteoporosis, alterations in cognition and mood, anemia, depression, anemia, hair loss, obesity, and endometriosis. In addition, female sex-organ cancers such as breast cancer, uterine cancer and ovarian cancer are hormone related.

Muscle wasting refers to the progressive loss of muscle mass and/or to the progressive weakening and degeneration of muscles, including the skeletal or voluntary muscles, which control movement, cardiac muscles, which control the heart (cardiomyopathics), and smooth muscles. Chronic muscle wasting is a chronic condition (i.e. persisting over a long period of time) characterized by progressive loss of muscle mass, weakening and degeneration of muscle. The loss of muscle mass that occurs during muscle wasting can be characterized by a muscle protein breakdown or degradation. Protein degradation occurs because of an unusually high rate of protein degradation, an unusually low rate of protein synthesis, or a combination of both. Protein degradation, whether caused by a high degree of protein degradation or a low degree of protein synthesis, leads to a decrease in muscle mass and to muscle wasting. Muscle wasting is associated with chronic, neurological, genetic or infectious pathologies, diseases, illnesses or conditions. These include Muscular Dystrophies such as Duchenne Muscular Dystrophy and Myotonic Dystrophy; Muscle Atrophies such as Post-Polio Muscle Atrophy (PPMA); Cachexias such as Cardiac Cachexia, AIDS Cachexia and Cancer Cachexia, malnutrition, Leprosy, Diabetes, Renal Disease, Chronic Obstructive Pulmonary Disease (COPD), Cancer, end stage Renal failure, Emphysema, Osteomalacia, HIV Infection, AIDS, and Cardiomyopathy, In addition, other circumstances and conditions are linked to and can cause muscle wasting. These include chronic lower back pain, advanced age, central nervous system (CNS) injury, peripheral nerve injury, spinal cord injury, chemical injury, central nervous system (CNS) damage, peripheral nerve damage, spinal cord damage, chemical damage, burns, disuse deconditioning that occurs when a limb is immobilized, long term hospitalization due to illness or injury, and alcoholism. Muscle wasting, if left unabated, can have dire health consequences. For example, the changes that occur during muscle wasting can lead to a weakened physical state that is detrimental to an individual's health, resulting in increased susceptibility to infection, poor performance status and susceptibility to injury.

New innovative approaches are urgently needed at both the basic science and clinical levels to develop compounds which are useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia, osteoporosis, and alterations in mood and cognition; c) treatment of conditions associated with Androgen Decline in Female (ADIF), such as sexual dysfunction, decreased sexual libido, hypogonadism, sarcopenia, osteopenia, osteoporosis, alterations in cognition and mood, depression, anemia, hair loss, obesity and endometriosis, d) treatment and/or prevention of chronic muscular wasting; e) decreasing the incidence of, halting or causing a regression of prostate cancer; f) oral androgen replacement; g) treatment and/or prevention of benign prostate hyperplasia (BPH); i) treatment and/or prevention of cancers of female sexual organs such as breast cancer, uterine cancer and ovarian cancer; and/or other clinical therapeutic and/or diagnostic areas.

Tucker et al (*J. Med Chem* (1988), 31, 885-887; and *J. Med Chem* (1988), 31, 954-959) discloses the synthesis and resolution of 4'cyano-3-[(4-fluorophenyl)sulphonyl)[-2-hydroxy-2-methyl-3'-(trifluoromethyl) propionamide (bicalutamide), a non-steroidal antiandrogen useful in the treatment of advanced prostate cancer. Tucker (U.S. Pat. No. 4,636,505) discloses N-(substituted phenyl)-3-alkyl-, aryl- and heteroarylsulfonyl-2-hydroxy-2-alkyl- and haloalkylpropanamide compounds, methods for their preparation, and their utility in the treatment of malignant or benign prostatic disease or of androgen dependent disease conditions. Kirkovsky et al (*J. Med Chem* (2000), 43, 581-590) discloses the synthesis of chiral non-steroidal affinity ligands which are bicalutamide analogues bearing electrophillic groups in the B aromatic ring. Miller et al (U.S. Pat. Nos. 6,160,011 and 6,071,957) discloses the non-steroidal agonist compounds, their preparation and their use in male hormone therapy and in the treatment of prostate cancer. These references all teach methods of preparing non-steroidal agonist compounds having a thio, sulfoxide or sulfone linkage. In addition, the processes disclosed in these references are not suitable for large-scale preparation, since one or more of the steps result in mixtures of products, and thus involve purification procedures which ultimately result in a lower yield.

There is a need in the art to develop synthetic methods for the synthesis of non-steroidal agonist compounds, that can be used for large-scale synthesis, and that provide highly pure products in high yield.

SUMMARY OF THE INVENTION

In one embodiment, present invention relates to a synthetic process for the preparation of a novel class of androgen receptor targeting agents (ARTA), which demonstrate androgenic and anabolic activity of a nonsteroidal ligand for the androgen receptor. The agents define a new subclass of compounds, which are selective androgen receptor modulators (SARMs) useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia, osteoporosis, and alterations in mood and cognition; c) treatment of conditions associated with Androgen Decline in Female (ADIF), such as sexual dysfunction, decreased sexual libido, hypogonadism, sarcopenia, osteopenia, osteoporosis, alterations in cognition and mood, depression, anemia, hair loss, obesity and endometriosis, d) treatment and/or prevention of chronic muscular wasting; e) decreasing the incidence of, halting or causing a regression of prostate cancer; f) oral androgen replacement; g) preventing and/or treating dry eye conditions; h) treatment and/or prevention of benign prostate hyperplasia (BPH); i) inducing apoptosis in a cancer cell; j) treatment and/or prevention of cancers of female sexual organs such as breast cancer, uterine cancer and ovarian cancer; and/or other clinical therapeutic and/or diagnostic areas.

The process of the present invention is suitable for large-scale preparation, since all of the steps give rise to highly pure compounds, thus avoiding complicated purification procedures which ultimately lower the yield. Thus the present invention provides methods for the synthesis of non-steroidal agonist compounds, that can be used for industrial large-scale synthesis, and that provide highly pure products in high yield.

In one embodiment, the present invention provides a process for preparing a selective androgen receptor modulator (SARM) compound represented by the structure of formula I:

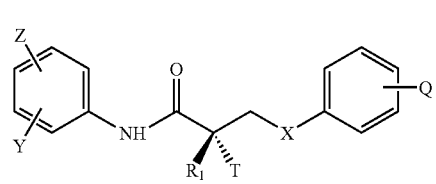

wherein
X is O, NH, Se, PR, or NR;
T is OH, OR, NHCOCH$_3$, or NHCOR;
Z is NO$_2$, CN, COOH, COR, NHCOR or CONHR;
Y is CF$_3$, F, I, Br, Cl, CN, CR$_3$ or SnR$_3$;
Q is alkyl, halogen, CF$_3$, CN CR$_3$, SnR$_3$, NR$_2$, NHCOCH$_3$, NHCOCF$_3$, NHCOR, NHCONHR, NHCOOR, OCONHR, CONHR, NHCSCH$_3$, NHCSCF$_3$, NHCSR NHSO$_2$CH$_3$, NHSO$_2$R, OR, COR, OCOR, OSO$_2$R, SO$_2$R, SR; or Q together with the benzene ring to which it is attached is a fused ring system represented by structure A, B or C:

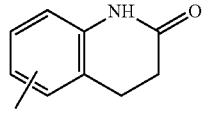
A

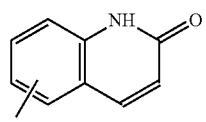
B

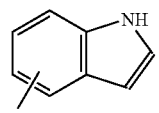
C

R is alkyl, haloalkyl, dihaloalkyl, trihaloalkyl, CH$_2$F, CHF$_2$, CF$_3$, CF$_2$CF$_3$, aryl, phenyl, halogen, alkenyl or OH; and R$_1$ is CH$_3$, CH$_2$F, CHF$_2$, CF$_3$, CH$_2$CH$_3$, or CF$_2$CF$_3$;

the process comprising the steps of:

coupling an amide of formula II:

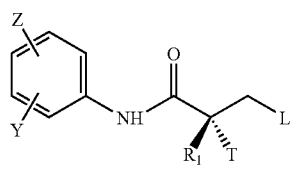
II wherein Z, Y R$_1$ and T are as defined above and L is a leaving group, with a compound of formula III:

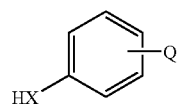
III wherein Q and X are as defined above, thereby producing the compound of formula I; and purifying the compound of formula I using a mixture of alcohol and water.

In one embodiment, the coupling step is carried out in the presence of a base. In another embodiment, the leaving group L is Br.

In one embodiment, the alcohol is ethanol. In another embodiment, the purification step comprises crystallizing the compound of formula I from the mixture of ethanol and water. In another embodiment, the crystallization step comprises mixing an ethanol solution comprising compound I with water, so as to crystallize the compound of formula I. In another embodiment, the process further comprises the step of collecting the compound of formula I by filtration.

In one embodiment, the amide of formula II is prepared by
a) converting a cyclic compound of formula IX wherein L and R$_1$ are as defined above and T$_1$ is O or NH, to a compound of formula VIII wherein L and R$_1$ are as defined above and T$_2$ is OH or NH$_2$;

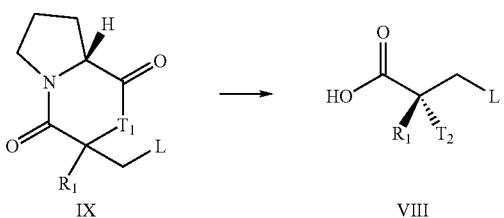
IX        VIII b) reacting an amine of formula VII:

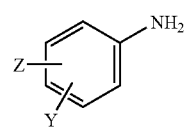
VII wherein Z and Y are as defined above, with the carboxylic acid of formula VIII in the presence of a coupling reagent, to produce an amide of formula IIA; and

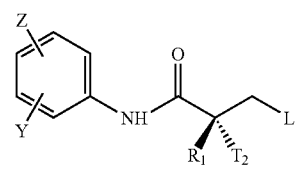
IIA c) optionally converting T$_2$ to T.

In one embodiment, step (a) is carried out in the presence of HBr.

Furthermore, in another embodiment, the present invention provides a process for preparing a selective androgen receptor modulator (SARM) compound represented by the structure of formula I:

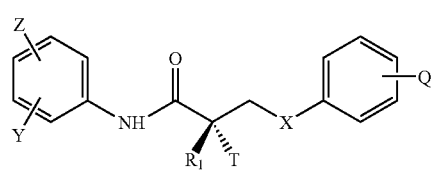
I wherein
X is O, NH, Se, PR, or NR;
T is OH, OR, NHCOCH$_3$, or NHCOR;
Z is NO$_2$, CN, COOH, COR, NHCOR or CONHR;
Y is CF$_3$, F, I, Br, Cl, CN, CR$_3$ or SnR$_3$;
Q is alkyl, halogen, CF$_3$, CN CR$_3$, SnR$_3$, NR$_2$, NHCOCH$_3$, NHCOCF$_3$, NHCOR, NHCONHR, NHCOOR, OCONHR, CONHR, NHCSCH$_3$, NHCSCF$_3$, NHCSR NHSO$_2$CH$_3$, NHSO$_2$R, OR, COR, OCOR, OSO$_2$R, SO$_2$R, SR; or Q together with the benzene ring to which it is attached is a fused ring system represented by structure A, B or C:

9

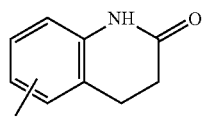
A

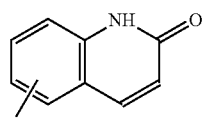
B

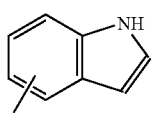
C

R is alkyl, haloalkyl, dihaloalkyl, trihaloalkyl, $CH_2F$, $CHF_2$, $CF_3$, $CF_2CF_3$, aryl, phenyl, halogen, alkenyl or OH; and $R_1$ is $CH_3$, $CH_2F$, $CHF_2$, $CF_3$, $CH_2CH_3$, or $CF_2CF_3$;

the process comprising the steps of:

a) converting a cyclic compound of formula IX wherein $R_1$ is as defined above, L is a leaving group, and $T_1$ is O or NH, to a compound of formula VIII wherein L and $R_1$ are as defined above and $T_2$ is OH or $NH_2$;

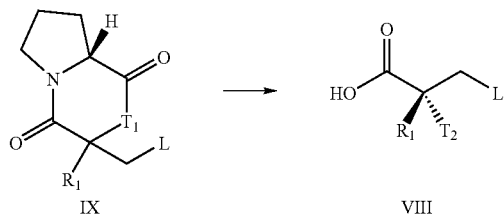

IX → VIII b) reacting an amine of formula VII:

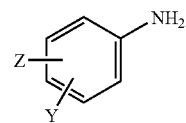
VII wherein Z and Y are as defined above, with the carboxylic acid of formula VIII in the presence of a coupling reagent, to produce an amide of formula IIA;

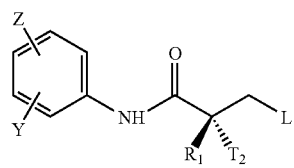
IIA c) optionally converting $T_2$ to T to generate a compound of formula II;

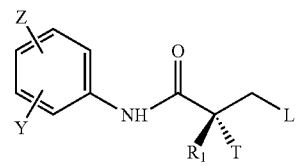
II d) coupling the amide of formula II with a compound of formula III:

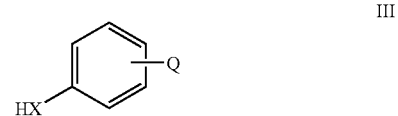
III wherein Q and X are as defined above, thereby obtaining the compound of formula I; and e) purifying the obtained compound of formula I using a mixture of ethanol and water.

In one embodiment, the present invention provides a process for preparing a selective androgen modulator compound of formula I wherein is X is O. In another embodiment, the present invention provides a process for preparing a selective androgen modulator compound of formula I wherein is T is OH. In another embodiment, the present invention provides a process for preparing a selective androgen modulator compound of formula I wherein is $R_1$ is $CH_3$. In another embodiment, the present invention provides a process for preparing a selective androgen modulator compound of formula I wherein Z is $NO_2$. In another embodiment, the present invention provides a process for preparing a selective androgen modulator compound of formula I wherein Z is CN. In another embodiment, the present invention provides a process for preparing a selective androgen modulator compound of formula I wherein Y is $CF_3$. In another embodiment, the present invention provides a process for preparing a selective androgen modulator compound of formula I wherein Q is $NHCOCH_3$. In another embodiment, the present invention provides a process for preparing a selective androgen modulator compound of formula I wherein Q is F.

In another embodiment, the present invention provides a process for preparing a selective androgen modulator compound represented by the structure of formula IV:

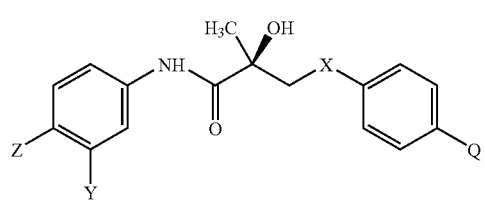
IV

In another embodiment, the present invention provides a process for preparing a selective androgen modulator compound represented by the structure of formula (1):

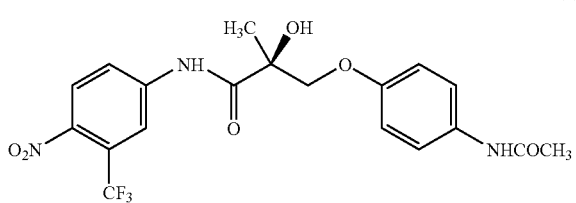

(1)

In another embodiment, the present invention provides a process for preparing a selective androgen modulator compound represented by the structure of formula (2):

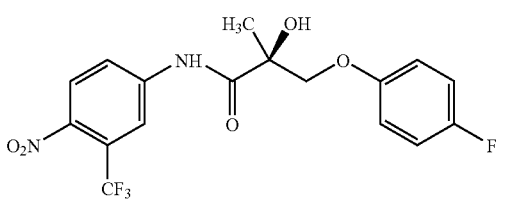

(2)

In another embodiment, the present invention provides a process for preparing a selective androgen modulator compound represented by the structure of formula (3):

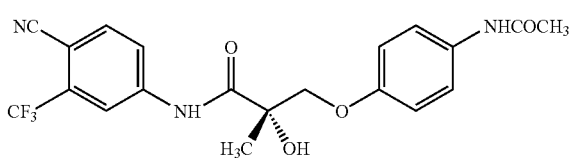

(3)

In another embodiment, the present invention provides a process for preparing a selective androgen modulator compound represented by the structure of formula (4):

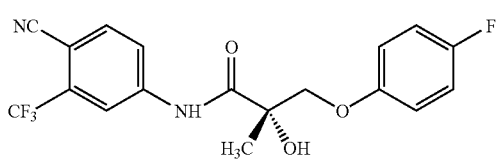

(4)

In another embodiment, the process further comprises the step of converting the selective androgen receptor modulator (SARM) compound to its analog, derivative, isomer, metabolite, pharmaceutically acceptable salt, pharmaceutical product, hydrate, N-oxide, prodrug, polymorph, crystal or any combination thereof. In another embodiment, the SARM compound has in-vivo androgenic and anabolic activity of a nonsteroidal ligand for the androgen receptor.

The novel selective androgen receptor modulator compounds of the present invention, either alone or as a pharmaceutical composition, are useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia, osteoporosis, and alterations in mood and cognition; c) treatment of conditions associated with Androgen Decline in Female (ADIF), such as sexual dysfunction, decreased sexual libido, hypogonadism, sarcopenia, osteopenia, osteoporosis, alterations in cognition and mood, depression, anemia, hair loss, obesity and endometriosis, d) treatment and/or prevention of chronic muscular wasting; e) decreasing the incidence of, halting or causing a regression of prostate cancer; g) preventing and/or treating dry eye conditions; h) treatment and/or prevention of benign prostate hyperplasia (BPH); i) inducing apoptosis in a cancer cell; j) treatment and/or prevention of cancers of female sexual organs such as breast cancer, uterine cancer and ovarian cancer; and/or other clinical therapeutic and/or diagnostic areas.

The selective androgen receptor modulator compounds of the present invention offer a significant advancement over steroidal androgen treatment because the selective androgen receptor modulator compounds of the present invention have been shown in-vivo to have an androgenic and anabolic activity of a nonsteroidal ligand for the androgen receptor. Thus, the selective androgen receptor modulator compounds have an androgenic and anabolic activity of a nonsteroidal ligand for the androgen receptor and will not be accompanied by serious side effects, inconvenient modes of administration, or high costs and still have the advantages of oral bioavailability, lack of cross-reactivity with other steroid receptors, and long biological half-lives.

DETAILED DESCRIPTION OF THE INVENTION

In one embodiment, the present invention provides a synthetic process for the preparation of a novel class of androgen receptor targeting agents (ARTA), which demonstrate androgenic and anabolic activity of a nonsteroidal ligand for the androgen receptor. The agents define a new subclass of compounds which are selective androgen receptor modulators (SARM) which are useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia, osteoporosis, and alterations in mood and cognition; c) treatment of conditions associated with Androgen Decline in Female (ADIF), such as sexual dysfunction, decreased sexual libido, hypogonadism, sarcopenia, osteopenia, osteoporosis, alterations in cognition and mood, depression, anemia, hair loss, obesity and endometriosis, d) treatment and/or prevention of chronic muscular wasting; e) decreasing the incidence of, halting or causing a regression of prostate cancer; f) oral androgen replacement; g) preventing and/or treating dry eye conditions; h) treatment and/or prevention of benign prostate hyperplasia (BPH); i) inducing apoptosis in a cancer cell; j) treatment and/or prevention of cancers of female sexual organs such as breast cancer, uterine cancer and ovarian cancer; and/or other clinical therapeutic and/or diagnostic areas.

In copending U.S. application Ser. No. 10/277,108, assigned to the Assignees of the present invention, Applicants disclose a process for preparing selective androgen receptor modulator (SARM) compounds. In the disclosed process, the SARM product is purified by using hexane as the purification solvent. However, hexane is known to be neurotoxic, as it is rapidly metabolized to 2,5-hexanedione. Thus, any residual solvents left after the synthesis could result in undesirable toxicity upon administration of the SARM compound.

As demonstrated herein, Applicants have surprisingly and unexpectedly found that when the purification step of the SARM compounds is carried out in the presence of a nontoxic organic solvent and water, such as ethanol and water, for example by recrystallization from a mixture of ethanol and water, a highly pure product with excellent crystal stability is obtained in high yields. In addition, the use of a nontoxic organic solvent/water for purification is safe and cheap, and avoids any biological hazards that may arise from the use of toxic organic solvents such as hexane. In one embodiment, the nontoxic organic solvent is ethanol.

Thus, in one embodiment, the present invention provides a synthetic process for preparing the SARM compounds described herein, which involves a purification step comprising crystallization of the SARM product using a mixture of a nontoxic organic solvent and water. In one embodiment, the nontoxic organic solvent is ethanol. In a particular embodiment, the crystallization step comprises mixing an ethanol solution comprising the SARM compound with water, so as to crystallize the SARM compound. In a further embodiment, the process further comprises the step of collecting the SARM compound by filtration.

The process of the present invention is suitable for large-scale preparation, since all of the steps give rise to highly pure compounds, thus avoiding complicated purification procedures which ultimately lower the yield. Thus the present invention provides methods for the synthesis of non-steroidal agonist compounds, that can be used for industrial large-scale synthesis, and that provide highly pure products in high yield. In addition, the methods described by the present invention utilize safe, environmentally friendly and cheap reagents and purification steps, thus avoiding any undesirable toxicological issues that may arise from the use of toxic, environmentally unfriendly or biologically unstable reagents.

It should be apparent to a person skilled in the art that any nontoxic organic solvent is suitable in the methods of the present invention, for example alcohols such as methanol or ethanol, aromatic compounds such as toluene and xylene, DMSO, THF, ethyl acetate, methyl-t-butyl ether, heptane, cyclohexane and the like. In addition, any combination of such solvents is suitable for use in the methods of the present invention, such as ethyl acetate/heptane, tetrahyrofuran (THF)/Heptane, ethyl acetate/methyl-t-butyl ether (MTBE), THF/MTBE and the like.

In one embodiment, the nontoxic organic solvent is ethanol. Any grade and purity level of ethanol is suitable. In one embodiment, the ethanol is neat ethanol. In another embodiment, the ethanol is an ethanol solution that contains denaturants, such as toluene, methanol and the like. For example, a suitable ethanol grade, is ethanol containing the denaturants toluene (5%), methanol (5%, 10%), isopropanol (5%), ethyl acetate (1%, 4%), acetone (7%), gasoline or any combination of such denaturants.

Accordingly, In one embodiment, the present invention provides a process for preparing a selective androgen receptor modulator (SARM) compound represented by the structure of formula I:

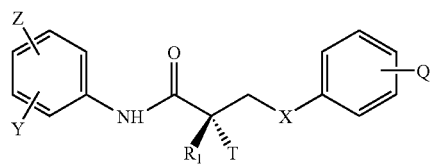

wherein
X is O, NH, Se, PR, or NR;
T is OH, OR, NHCOCH$_3$, or NHCOR;
Z is NO$_2$, CN, COOH, COR, NHCOR or CONHR;
Y is CF$_3$, F, I, Br, Cl, CN, CR$_3$ or SnR$_3$;
Q is alkyl, halogen, CF$_3$, CN CR$_3$, SnR$_3$, NR$_2$, NHCOCH$_3$, NHCOCF$_3$, NHCOR, NHCONHR, NHCOOR, OCONHR, CONHR, NHCSCH$_3$, NHCSCF$_3$, NHCSR NHSO$_2$CH$_3$, NHSO$_2$R, OR, COR, OCOR, OSO$_2$R, SO$_2$R, SR; or Q together with the benzene ring to which it is attached is a fused ring system represented by structure A, B or C:

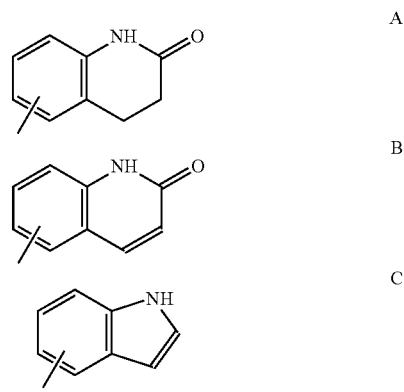

R is alkyl, haloalkyl, dihaloalkyl, trihaloalkyl, CH$_2$F, CHF$_2$, CF$_3$, CF$_2$CF$_3$, aryl, phenyl, halogen, alkenyl or OH; and
R$_1$ is CH$_3$, CH$_2$F, CHF$_2$, CF$_3$, CH$_2$CH$_3$, or CF$_2$CF$_3$;
the process comprising the steps of:
coupling an amide of formula II:

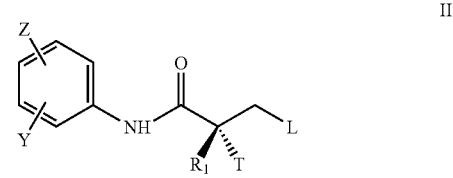

wherein Z, Y R$_1$ and T are as defined above and L is a leaving group, with a compound of formula III:

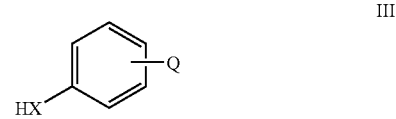

wherein Q and X are as defined above, thereby producing the compound of formula I; and
purifying the compound of formula I using a mixture of alcohol and water.

In one embodiment, the alcohol is ethanol. In another embodiment, the purification step comprises crystallizing the compound of formula I from the mixture of ethanol and water. In another embodiment, the crystallization step comprises mixing an ethanol solution comprising compound I with water, so as to crystallize the compound of formula I. In another embodiment, the process further comprises the step of collecting the compound of formula I by filtration.

In one embodiment, the amide of formula II is prepared by
a) converting a cyclic compound of formula IX wherein L and $R_1$ are as defined above and $T_1$ is O or NH, to a compound of formula VIII wherein L and $R_1$ are as defined above and $T_2$ is OH or $NH_2$;

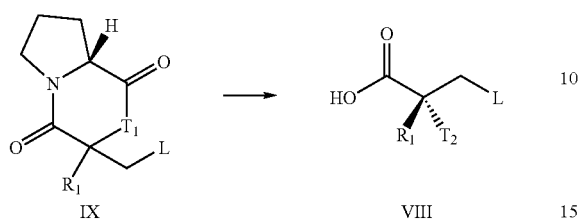

b) reacting an amine of formula VII:

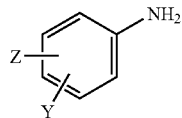

wherein Z and Y are as defined above, with the carboxylic acid of formula VIII in the presence of a coupling reagent, to produce an amide of formula IIA; and

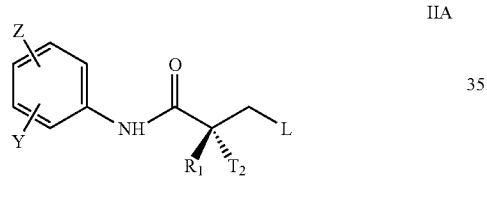

c) optionally converting $T_2$ to T.

In one embodiment, step (a) is carried out in the presence of HBr.

Furthermore, in another embodiment, the present invention provides a process for preparing a selective androgen receptor modulator (SARM) compound represented by the structure of formula I:

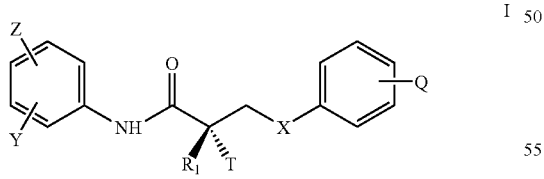

wherein
X is O, NH, Se, PR, or NR;
T is OH, OR, $NHCOCH_3$, or NHCOR;
Z is $NO_2$, CN, COOH, COR, NHCOR or CONHR;
Y is $CF_3$, F, I, Br, Cl, CN, $CR_3$ or $SnR_3$;
Q is alkyl, halogen, $CF_3$, CN $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$, SR; or Q together with the benzene ring to which it is attached is a fused ring system represented by structure A, B or C:

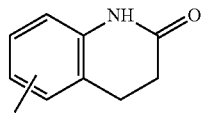

A

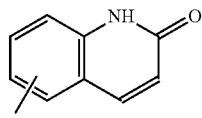

B

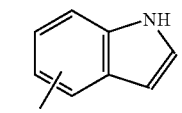

C

R is alkyl, haloalkyl, dihaloalkyl, trihaloalkyl, $CH_2F$, $CHF_2$, $CF_3$, $CF_2CF_3$, aryl, phenyl, halogen, alkenyl or OH; and $R_1$ is $CH_3$, $CH_2F$, $CHF_2$, $CF_3$, $CH_2CH_3$, or $CF_2CF_3$;

the process comprising the steps of:

a) converting a cyclic compound of formula IX wherein $R_1$ is as defined above, L is a leaving group, and $T_1$ is O or NH, to a compound of formula VIII wherein L and $R_1$ are as defined above and $T_2$ is OH or $NH_2$;

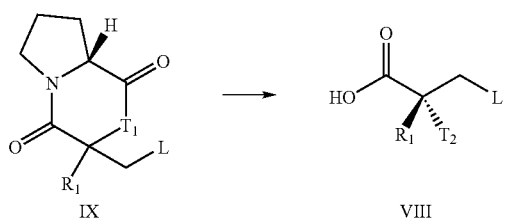

b) reacting an amine of formula VII:

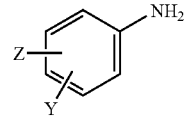

wherein Z and Y are as defined above, with the carboxylic acid of formula VIII in the presence of a coupling reagent, to produce an amide of formula IIA;

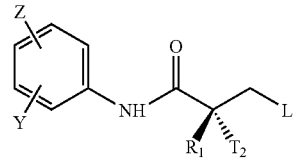

c) optionally converting $T_2$ to T to generate a compound of formula II;

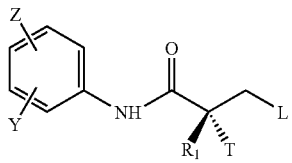

II d) coupling the amide of formula II with a compound of formula III:

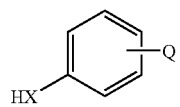

III wherein Q and X are as defined above; and e) purifying the obtained compound of formula I using a mixture of ethanol and water.

It is understood to a person skilled in the art that when $T_1$ in compound IX is O or NH, $T_2$ in compound VIII is OH or $NH_2$, respectively. Accordingly, in the case that T is OR, $NHCOCH_3$ or NHCOCHR, the reaction will further involve the conversion of $T_2$ to these moieties. Thus, when T in compound I is OR, the reaction will involve a further step of converting the OH to OR by a reaction with, for example, an alkyl halide R—X. When T in compound I is NHCOR, $NHCOCH_3$, the reaction will involve a further step of converting the $NH_2$ to NHCOR or $NHCOCH_3$, by a reaction with, for example, the corresponding acyl chloride ClCOR or ClCOCH$_3$.

It is understood by a person skilled in the art that the amount of water and ethanol used can be optimized to yield the highest yield of crystallized SARM product, and/or the SARM product with the highest crystal stability and quality. For example, without being bound to any particular embodiment, the ratio of ethanol to water is 20:1. In another embodiment, the ratio is 15:1. In another embodiment, the ratio is 10:1. In another embodiment, the ratio is 8:1. In another embodiment, the ratio is 5:1. In another embodiment, the ratio is 3:1. In another embodiment is 2:1. In another embodiment, the ratio is 1:1. In another embodiment, the ratio of water to ethanol is 20:1. In another embodiment, the ratio is 15:1. In another embodiment, the ratio is 10:1. In another embodiment, the ratio is 8:1. In another embodiment, the ratio is 5:1. In another embodiment, the ratio is 3:1. In another embodiment is 2:1.

In addition, the order in which the ethanol and water are mixed may be optimized to yield the highest yield and/or quality of SARM compound. For example, in one embodiment, an ethanol solution comprising the SARM compound may be poured on to water, or may be added slowly to water. In another embodiment, water may be added slowly, in aliquots or in one aliquot to an ethanol solution comprising the SARM compound.

In addition, other parameters such as crystallization time, temperature etc. may be varied in order to yield the optimal results. For example, the crystallization temperature may be 0° C., (−)10-0° C., 0-5° C., 5°10° C., 10C.-20° C., or at room temperature (20-25° C.). The crystallization times may range from minutes to hours to days, depending on the particular conditions used.

In one embodiment, the present invention provides a process for preparing a selective androgen modulator compound of formula I wherein is X is O. In another embodiment, the present invention provides a process for preparing a selective androgen modulator compound of formula I wherein is T is OH. In another embodiment, the present invention provides a process for preparing a selective androgen modulator compound of formula I wherein is $R_1$ is $CH_3$. In another embodiment, the present invention provides a process for preparing a selective androgen modulator compound of formula I wherein Z is $NO_2$. In another embodiment, the present invention provides a process for preparing a selective androgen modulator compound of formula I wherein Z is CN. In another embodiment, the present invention provides a process for preparing a selective androgen modulator compound of formula I wherein Y is $CF_3$. In another embodiment, the present invention provides a process for preparing a selective androgen modulator compound of formula I wherein Q is $NHCOCH_3$. In another embodiment, the present invention provides a process for preparing a selective androgen modulator compound of formula I wherein Q is F.

In another embodiment, the present invention provides a process for preparing a selective androgen modulator compound represented by the structure of formula IV:

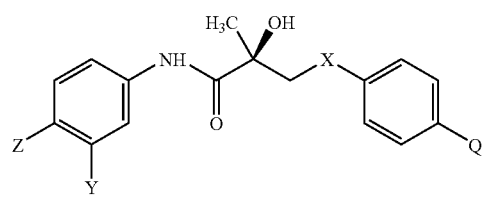

IV

In another embodiment, the present invention provides a process for preparing a selective androgen modulator compound represented by the structure of formula (1):

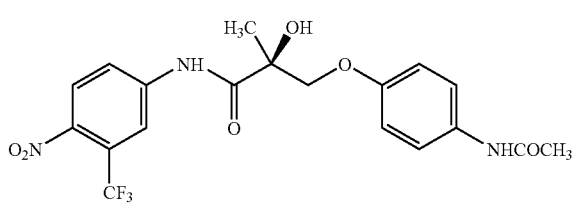

(1)

In another embodiment, the present invention provides a process for preparing a selective androgen modulator compound represented by the structure of formula (2):

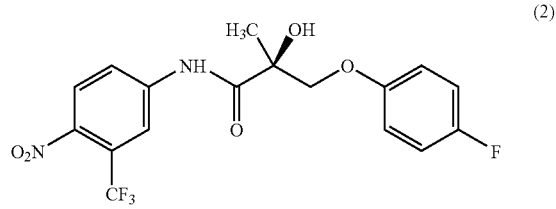

(2)

In another embodiment, the present invention provides a process for preparing a selective androgen modulator compound represented by the structure of formula (3):

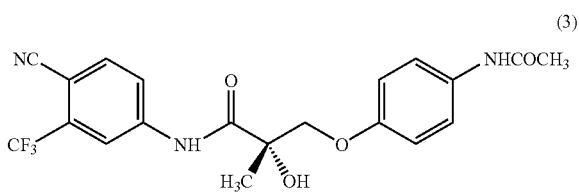

(3)

In another embodiment, the present invention provides a process for preparing a selective androgen modulator compound represented by the structure of formula (4):

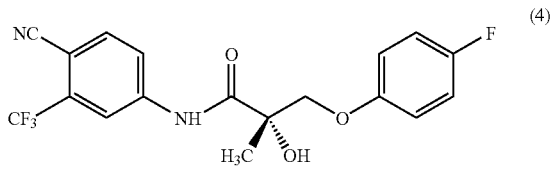

(4)

In another embodiment, the present invention provides a process for preparing a selective androgen modulator compound represented by the structure of formula XV:

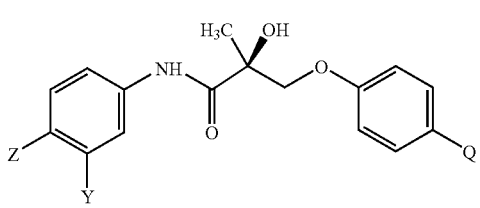

XV

In one embodiment, the coupling of compounds II and III is carried out in the presence of a base. Any suitable base that will deprotonate the hydrogen of the -XH moiety (for example, a phenol moiety when X is O) and allow the coupling may be used. Nonlimiting examples of bases are carbonates such as alkali carbonates, for example sodium carbonate ($Na_2CO_3$), potassium carbonate ($K_2CO_3$) and cesium carbonate ($Cs_2CO_3$); bicarbonates such as alkali metal bicarbonates, for example sodium bicarbonate ($NaHCO_3$), potassium bicarbonate ($KHCO_3$), alkali metal hydrides such as sodium hydride (NaH), potassium hydride (KH) and lithium hydride (LiH), and the like.

The leaving group L is defined herein as any removable group customarily considered for chemical reactions, as will be known to the person skilled in the art. Suitable leaving groups are halogens, for example F, Cl, Br and I; alkyl sulfonate esters (—$OSO_2R$) wherein R is an alkyl group, for example methanesulfonate (mesylate), trifluoromethanesulfonate, ethanesulfonate, 2,2,2-trifluoroethanesulfonate, perfluoro butanesulfonate; aryl sulfonate esters (—$OSO_2Ar$) wherein Ar is an aryl group, for example p-toluoylsulfonate (tosylate), benzenesulphonate which may be unsubstituted or substituted by methyl, chlorine, bromine, nitro and the like; $NO_3$, $NO_2$, or sulfate, sulfite, phosphate, phosphite, carboxylate, imino ester, $N_2$ or carbamate.

The reaction is conveniently carried out in a suitable inert solvent or diluent such as, for example, tetrahyrofuran, diethyl ether, aromatic amines such as pyridine; aliphatic and aromatic hydrocarbons such as benzene, toluene, and xylene; dimethylsulfoxide (DMSO), dimethylformamide (DMF), and dimethylacetamide (DMAC). The reaction is suitably carried out at a temperature in the range, for example, −20 to 120 C., for example at or near ambient temperature.

The coupling reagent is a reagent capable of turning the carboxylic acid VIII into a reactive derivative thereof, thus enabling coupling with amine (VIII) to form an amide bond. A suitable reactive derivative of a carboxylic acid is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol, an ester such as pentafluorophenyl trifluoroacetate or an alcohol such as methanol, ethanol, isopropanol, butanol or N-hydroxybenzotriazole; an acyl azide, for example an azide formed by the reaction of the acid and azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide.

The reaction is conveniently carried out in a suitable inert solvent or diluent as described hereinabove, suitably in the presence of a base such as triethylamine, and at a temperature in the range, as described above.

Furthermore, in another embodiment, the present invention provides a process for preparing a selective androgen receptor modulator (SARM) compound having in-vivo androgenic and anabolic activity of a nonsteroidal ligand for the androgen receptor, the compound represented by the structure of formula X:

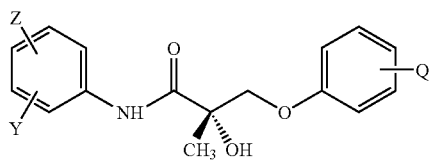

X wherein

Z is $NO_2$, CN, COOH, COR, NHCOR or CONHR;

Y is $CF_3$, F, I, Br, Cl, CN, $CR_3$ or $SnR_3$;

Q is alkyl, halogen, $CF_3$, CN $CR_3$, $SnR_3$, $NR_2$, $NHCOCH_3$, $NHCOCF_3$, NHCOR, NHCONHR, NHCOOR, OCONHR, CONHR, $NHCSCH_3$, $NHCSCF_3$, NHCSR $NHSO_2CH_3$, $NHSO_2R$, OR, COR, OCOR, $OSO_2R$, $SO_2R$, SR; or Q together with the benzene ring to which it is attached is a fused ring system represented by structure A, B or C:

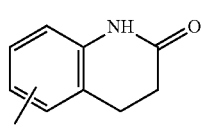

A

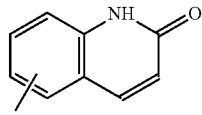

B

-continued

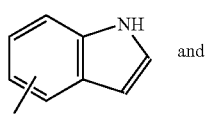 and

R is alkyl, haloalkyl, dihaloalkyl, trihaloalkyl, $CH_2F$, $CHF_2$, $CF_3$, $CF_2CF_3$, aryl, phenyl, halogen, alkenyl or OH;

the process comprising the steps of:

a) preparing a carboxylic acid of formula XII by ring opening of a cyclic compound of formula XI

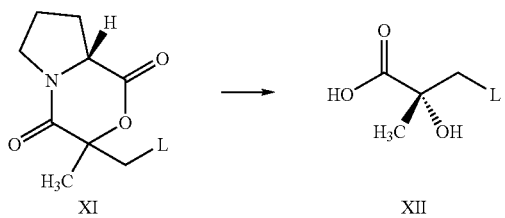

wherein L is as defined above;

b) reacting an amine of formula VII:

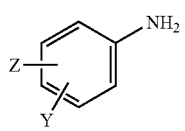

wherein Z and Y are as defined above, with the carboxylic acid of formula XII in the presence of a coupling reagent, to produce an amide of formula XIII

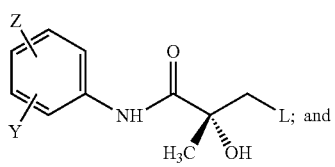

c) coupling the amide of formula XIII with a phenol of formula XIV:

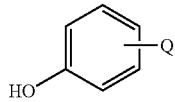

wherein Q is as defined above; and purifying the compound of formula X using a mixture of ethanol and water. In one embodiment, step (a) is carried out in the presence of HBr.

In accordance with this particular embodiment, the process is carried out according to the following prototype synthetic scheme (exemplified by Q=acetamido):

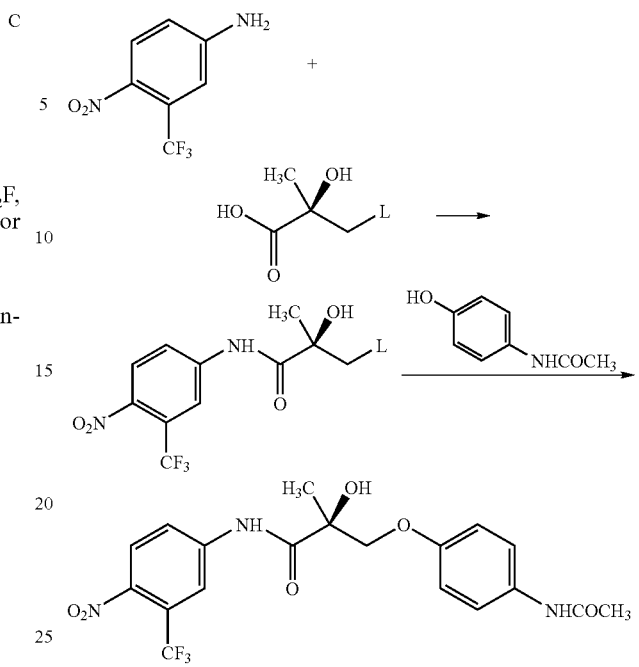

In one embodiment, the SARM compound has in-vivo androgenic and anabolic activity of a nonsteroidal ligand for the androgen receptor.

The substituent R is defined herein as an alkyl, haloalkyl, dihaloalkyl, trihaloalkyl, $CH_2F$, $CHF_2$, $CF_3$, $CF_2CF_3$; aryl, phenyl, halogen, alkenyl, or hydroxyl (OH).

An "alkyl" group refers to a saturated aliphatic hydrocarbon, including straight-chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

A "haloalkyl" group refers to an alkyl group as defined above, which is substituted by one or more halogen atoms, e.g. by F, Cl, Br or I.

An "aryl" group refers to an aromatic group having at least one carbocyclic aromatic group or heterocyclic aromatic group, which may be unsubstituted or substituted by one or more groups selected from halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

A "hydroxyl" group refers to an OH group. An "alkenyl" group refers to a group having at least one carbon to carbon double bond. A halo group refers to F, Cl, Br or I.

An "arylalkyl" group refers to an alkyl bound to an aryl, wherein alkyl and aryl are as defined above. An example of an aralkyl group is a benzyl group.

In another embodiment, the process further comprises the step of converting the selective androgen receptor modulator (SARM) compound to its analog, derivative, isomer, metabolite, pharmaceutically acceptable salt, pharmaceutical product, hydrate, N-oxide, prodrug, polymorph, crystal or any combination thereof. Thus, in one embodiment, the present invention provides a process for preparing an analog of a selective androgen modulator compound of formula (I). In another embodiment, this invention provides a process for preparing an isomer of a selective androgen modulator compound of formula (I). In another embodiment, this invention provides a process for preparing a metabolite of a selective androgen modulator compound of formula (I). In another embodiment, this invention provides a process for preparing a derivative of a selective androgen modulator compound of formula (I). In another embodiment, this invention provides a process for preparing a pharmaceutically acceptable salt of a selective androgen modulator compound of formula (I). In another embodiment, this invention provides a process for preparing a pharmaceutical product of a selective androgen modulator compound of formula (I). In another embodiment, this invention provides a process for preparing an N-oxide of a selective androgen modulator compound of formula (I). In another embodiment, this invention provides a process for preparing a prodrug of a selective androgen modulator compound of formula (I). In another embodiment, this invention provides a process for preparing a polymorph of a selective androgen modulator compound of formula (I). In another embodiment, this invention provides a process for preparing a crystal of a selective androgen modulator compound of formula (I). In another embodiment, this invention provides a process for preparing a hydrate of a selective androgen modulator compound of formula (I). In another embodiment, this invention provides a process for preparing a combination of any of analog, derivative, isomer, metabolite, pharmaceutically acceptable salt, pharmaceutical product, hydrate, N-oxide, prodrug, polymorph and/or crystal of a selective androgen modulator compound of formula (I).

Furthermore, in one embodiment, the present invention provides an analog of the compound of formula I, prepared in accordance with the process disclosed herein. In another embodiment, this invention provides an isomer of the compound of formula I, prepared in accordance with the process disclosed herein. In another embodiment, this invention provides a metabolite of the compound of formula I, prepared in accordance with the process disclosed herein. In another embodiment, this invention provides a derivative of the compound of formula I, prepared in accordance with the process disclosed herein. In another embodiment, this invention provides a pharmaceutically acceptable salt of the compound of formula I, prepared in accordance with the process disclosed herein. In another embodiment, this invention provides a pharmaceutical product of the compound of formula I, prepared in accordance with the process disclosed herein. In another embodiment, this invention provides an N-oxide of the compound of formula I, prepared in accordance with the process disclosed herein. In another embodiment, this invention provides a hydrate of the compound of formula I, prepared in accordance with the process disclosed herein. In another embodiment, this invention provides a prodrug of the compound of formula I, prepared in accordance with the process disclosed herein. In another embodiment, this invention provides a polymorph of the compound of formula I, prepared in accordance with the process disclosed herein. In another embodiment, this invention provides a crystal of the compound of formula I, prepared in accordance with the process disclosed herein. In another embodiment, this invention provides a combination of any of an analog, derivative, isomer, metabolite, pharmaceutically acceptable salt, pharmaceutical product, hydrate, N-oxide, prodrug, polymorph, crystal or N-oxide of the compound of formula I, prepared by the process disclosed herein.

As defined herein, the term "isomer" includes, but is not limited to, optical isomers and analogs, structural isomers and analogs, conformational isomers and analogs, and the like.

In one embodiment, this invention encompasses the use of various optical isomers of the SARM compounds. It will be appreciated by those skilled in the art that the SARM compounds of the present invention contain at least one chiral center. Accordingly, the SARM compounds used in the methods of the present invention may exist in, and be isolated in, optically-active or racemic forms. Some compounds may also exhibit polymorphism. It is to be understood that the present invention encompasses any racemic, optically-active, polymorphic, or stereroisomeric form, or mixtures thereof, which form possesses properties useful in the methods as described herein. In one embodiment, the SARM compounds are the pure (R)-isomers. In another embodiment, the SARM compounds are the pure (S)-isomers. In another embodiment, the SARM compounds are a mixture of the (R) and the (S) isomers. In another embodiment, the SARM compounds are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes pharmaceutically acceptable salts of amino-substituted compounds with organic and inorganic acids, for example, citric acid and hydrochloric acid. The invention also includes N-oxides of the amino substituents of the compounds described herein. Pharmaceutically acceptable salts can also be prepared from the phenolic compounds by treatment with inorganic bases, for example, sodium hydroxide. Also, esters of the phenolic compounds can be made with aliphatic and aromatic carboxylic acids, for example, acetic acid and benzoic acid esters.

This invention further includes derivatives of the SARM compounds. The term "derivatives" includes but is not limited to ether derivatives, acid derivatives, amide derivatives, ester derivatives and the like. In addition, this invention further includes hydrates of the SARM compounds. The term "hydrate" includes but is not limited to hemihydrate, monohydrate, dihydrate, trihydrate and the like.

This invention further includes metabolites of the SARM compounds. The term "metabolite" means any substance produced from another substance by metabolism or a metabolic process.

This invention further includes pharmaceutical products of the SARM compounds. The term "pharmaceutical product" means a composition suitable for pharmaceutical use (pharmaceutical composition), as defined herein.

This invention further includes prodrug of the SARM compounds. The term "prodrug" means a substance which can be converted in-vivo into a biologically active agent by such reactions as hydrolysis, esterification, desterification, activation, salt formation and the like.

This invention further includes crystals of the SARM compounds. Furthermore, this invention provides polymorphs of the SARM compounds. The term "crystal" means a substance in a crystalline state. The term "polymorph" refers to a particular crystalline state of a substance, having particular physical properties such as X-ray diffraction, IR spectra, melting point, and the like.

Biological Activity of Selective Androgen Modulator Compounds

The processes provided herein are useful in the preparation of a new subclass of compounds which are selective androgen receptor modulators (SARM). Several appropriately substituted SARMS have an unexpected in-vivo activity for an androgenic and anabolic activity of a nonsteroidal ligand for the androgen receptor. Further, appropriately substituted compounds are effective to treat prostate cancer and useful for imaging of prostate cancer.

As contemplated herein, the appropriately substituted SARM compounds of the present invention are useful for a) male contraception; b) treatment of a variety of hormone-related conditions, for example conditions associated with Androgen Decline in Aging Male (ADAM), such as fatigue, depression, decreased libido, sexual dysfunction, erectile dysfunction, hypogonadism, osteoporosis, hair loss, anemia, obesity, sarcopenia, osteopenia, osteoporosis, and alterations in mood and cognition; c) treatment of conditions associated with Androgen Decline in Female (ADIF), such as sexual dysfunction, decreased sexual libido, hypogonadism, sarcopenia, osteopenia, osteoporosis, alterations in cognition and mood, depression, anemia, hair loss, obesity and endometriosis, d) treatment and/or prevention of chronic muscular wasting; e) decreasing the incidence of, halting or causing a regression of prostate cancer; f) oral androgen replacement; g) preventing and/or treating dry eye conditions; h) treatment and/or prevention of benign prostate hyperplasia (BPH); i) inducing apoptosis in a cancer cell; j) treatment and/or prevention of cancers of female sexual organs such as breast cancer, uterine cancer and ovarian cancer; and/or other clinical therapeutic and/or diagnostic areas.

As used herein, receptors for extracellular signaling molecules are collectively referred to as "cell signaling receptors". Many cell signaling receptors are transmembrane proteins on a cell surface; when they bind an extracellular signaling molecule (i.e., a ligand), they become activated so as to generate a cascade of intracellular signals that alter the behavior of the cell. In contrast, in some cases, the receptors are inside the cell and the signaling ligand has to enter the cell to activate them; these signaling molecules therefore must be sufficiently small and hydrophobic to diffuse across the plasma membrane of the cell. As used herein, these receptors are collectively referred to as "intracellular cell signaling receptors".

Steroid hormones are one example of small hydrophobic molecules that diffuse directly across the plasma membrane of target cells and bind to intracellular cell signaling receptors. These receptors are structurally related and constitute the intracellular receptor superfamily (or steroid-hormone receptor superfamily). Steroid hormone receptors include progesterone receptors, estrogen receptors, androgen receptors, glucocorticoid type O receptors, and mineralocorticoid receptors. The present invention is particularly directed to androgen receptors.

In addition to ligand binding to the receptors, the receptors can be blocked to prevent ligand binding. When a substance binds to a receptor, the three-dimensional structure of the substance fits into a space created by the three-dimensional structure of the receptor in a ball and socket configuration.

The better the ball fits into the socket, the more tightly it is held. This phenomenon is called affinity. If the affinity of a substance is greater than the original hormone, it will compete with the hormone and bind the binding site more frequently. Once bound, signals may be sent through the receptor into the cells, causing the cell to respond in some fashion. This is called activation. On activation, the activated receptor then directly regulates the transcription of specific genes. But the substance and the receptor may have certain attributes, other than affinity, in order to activate the cell. Chemical bonds between atoms of the substance and the atoms of the receptors may form. In some cases, this leads to a change in the configuration of the receptor, which is enough to begin the activation process (called signal transduction). As a result, substances can be made which bind receptors and activate them (called receptor agonists) or inactivate them (called receptor antagonists). Examples of non-steroidal agonist are described in PCT International Patent Application Number PCT/US98/11020, International filing date May 28, 1998.

In one embodiment, the present invention is directed to processes for preparing selective androgen receptor modulator compounds which are agonist compounds. Thus, in one embodiment, the SARM compounds of the present invention are useful in binding to and activating steroidal hormone receptors. In one embodiment, the agonist compound of the present invention is an agonist which binds the androgen receptor. In another embodiment, the compound has high affinity for the androgen receptor. In another embodiment, the agonist compound also has anabolic activity. In another embodiment, the present invention provides selective androgen modulator compounds which have agonistic and anabolic activity of a nonsteroidal compound for the androgen receptor.

In one embodiment, the present invention is directed to processes for preparing selective androgen receptor modulator compounds which are antagonist compounds. Thus, in one embodiment, the SARM compounds of the present invention are useful in binding to and inactivating steroidal hormone receptors. In one embodiment, the antagonist compound of the present invention is an antagonist which binds the androgen receptor. In another embodiment, the compound has high affinity for the androgen receptor. In another embodiment, the antagonist compound also has anabolic activity. In another embodiment, the SARM compounds bind irreversibly to the androgen receptor. In another embodiment, the SARM compounds are alkylating agents.

In yet another embodiment, the SARM compounds of the present invention can be classified as partial AR agonist/antagonists. The SARMs are AR agonists in some tissues, and cause increased transcription of AR-responsive genes (e.g. muscle anabolic effect). In other tissues, these compounds serve as inhibitors at the AR to prevent agonistic effects of the native androgens.

Assays to determine whether the compounds of the present invention are AR agonists or antagonists are well known to a person skilled in the art. For example, AR agonistic activity can be determined by monitoring the ability of the SARM compounds to maintain and/or stimulate the growth of AR containing tissue such as prostate and seminal vesicles, as measured by weight. AR antagonistic activity can be determined by monitoring the ability of the SARM compounds to inhibit the growth of AR containing tissue.

The compounds of the present invention bind either reversibly or irreversibly to an androgen receptor. In one embodiment, the androgen receptor is an androgen receptor of a mammal. In another embodiment, the androgen receptor is an androgen receptor of a human. In one embodiment, the SARM compounds bind reversibly to the androgen receptor of a mammal, for example a human. Reversible binding of a compound to a receptor means that a compound can detach from the receptor after binding.

In another embodiment, the SARM compounds bind irreversibly to the androgen receptor of a mammal, for example a human. Thus, in one embodiment, the compounds of the present invention may contain a functional group (e.g. affinity label) that allows alkylation of the androgen receptor (i.e. covalent bond formation). Thus, in this case, the compounds are alkylating agents which bind irreversibly to the receptor and, accordingly, cannot be displaced by a steroid, such as the endogenous ligands DHT and testosterone. An "alkylating agent" is defined herein as an agent which alkylates (forms a covalent bond) with a cellular component, such as DNA, RNA or protein. It is a highly reactive chemical that introduces alkyl radicals into biologically active molecules and thereby prevents their proper functioning. The alkylating moiety is an electrophilic group that interacts with nucleophilic moieties in cellular components.

According to one embodiment of the present invention, a method is provided for binding the SARM compounds of the present invention to an androgen receptor by contacting the receptor with a SARM compound and/or its analog, derivative, isomer, metabolite, pharmaceutically acceptable salt, pharmaceutical product, hydrate or N-oxide or any combination thereof, under conditions effective to cause the selective androgen receptor modulator compound to bind the androgen receptor. The binding of the selective androgen receptor modulator compounds to the androgen receptor enables the compounds of the present invention to be useful as a male contraceptive and in a number of hormone therapies. The agonist compounds bind to and activate the androgen receptor. The antagonist compounds bind to and inactivate the androgen receptor. Binding of the agonist or antagonist compounds is either reversible or irreversible.

According to one embodiment of the present invention, a method is provided for suppressing spermatogenesis in a subject by contacting an androgen receptor of the subject with a SARM compound of the present invention and/or its analog, derivative, isomer, metabolite, pharmaceutically acceptable salt, pharmaceutical product, hydrate or N-oxide or any combination thereof, in an amount effective to bind the selective androgen receptor modulator compound to the androgen receptor and suppress spermatogenesis.

According to another embodiment of the present invention, a method is provided for contraception in a male subject, comprising the step of administering to the subject a SARM compound of the present invention and/or its analog, derivative, isomer, metabolite, pharmaceutically acceptable salt, pharmaceutical product, hydrate or N-oxide or any combination thereof, in an amount effective to suppress sperm production in the subject, thereby effecting contraception in the subject.

According to another embodiment of the present invention, a method is provided for hormonal therapy in a patient (i.e., one suffering from an androgen-dependent condition) which includes contacting an androgen receptor of a patient with a SARM compound of the present invention and/or its analog, derivative, isomer, metabolite, pharmaceutically acceptable salt, pharmaceutical product, hydrate or N-oxide or any combination thereof, in an amount effective to bind the selective androgen receptor modulator compound to the androgen receptor and effect a change in an androgen-dependent condition.

According to another embodiment of the present invention, a method is provided for hormone replacement therapy in a patient (i.e., one suffering from an androgen-dependent condition) which includes contacting an androgen receptor of a patient with a SARM compound of the present invention and/or its analog, derivative, isomer, metabolite, pharmaceutically acceptable salt, pharmaceutical product, hydrate or N-oxide or any combination thereof, in an amount effective to bind the selective androgen receptor modulator compound to the androgen receptor and effect a change in an androgen-dependent condition.

According to another embodiment of the present invention, a method is provided for treating a subject having a hormone related condition, which includes administering to the subject a SARM compound of the present invention and/or its analog, derivative, isomer, metabolite, pharmaceutically acceptable salt, pharmaceutical product, hydrate or N-oxide or any combination thereof, in an amount effective to bind the SARM compound to the androgen receptor and effect a change in an androgen-dependent condition.

Androgen-dependent conditions which may be treated according to the present invention include those conditions which are associated with aging, such as hypogonadism, sarcopenia, erythropoiesis, osteoporosis, and any other conditions later determined to be dependent upon low androgen (e.g., testosterone) levels.

According to another embodiment of the present invention, a method is provided for treating a subject suffering from prostate cancer, comprising the step of administering to the subject a SARM compound of the present invention and/or its analog, derivative, isomer, metabolite, pharmaceutically acceptable salt, pharmaceutical product, hydrate or N-oxide or any combination thereof, in an amount effective to treat prostate cancer in the subject.

According to another embodiment of the present invention, a method is provided for preventing prostate cancer in a subject, comprising the step of administering to the subject a SARM compound of the present invention and/or its analog, derivative, isomer, metabolite, pharmaceutically acceptable salt, pharmaceutical product, hydrate or N-oxide or any combination thereof, in an amount effective to treat prevent prostate cancer in the subject.

According to another embodiment of the present invention, a method is provided for delaying the progression of prostate cancer in a subject suffering from prostate cancer, comprising the step of administering to the subject a SARM compound of the present invention and/or its analog, derivative, isomer, metabolite, pharmaceutically acceptable salt, pharmaceutical product, hydrate or N-oxide or any combination thereof, in an amount effective to delay the progression of prostate cancer in the subject.

According to another embodiment of the present invention, a method is provided for preventing the recurrence of prostate cancer in a subject suffering from prostate cancer, comprising the step of administering to the subject a SARM compound of the present invention and/or its analog, derivative, isomer, metabolite, pharmaceutically acceptable salt, pharmaceutical product, hydrate or N-oxide or any combination thereof, in an amount effective to prevent the recurrence of prostate cancer in the subject.

According to another embodiment of the present invention, a method is provided for treating the recurrence of prostate cancer in a subject suffering from prostate cancer, comprising the step of administering to the subject a SARM compound of the present invention and/or its analog, derivative, isomer, metabolite, pharmaceutically acceptable salt, pharmaceutical product, hydrate or N-oxide or any combination thereof, in an amount effective to treat the recurrence of prostate cancer in the subject.

As defined herein, "contacting" means that the SARM compound of the present invention is introduced into a sample containing the enzyme in a test tube, flask, tissue culture, chip, array, plate, microplate, capillary, or the like, and incubated at a temperature and time sufficient to permit binding of the SARM to the enzyme. Methods for contacting the samples with the SARM or other specific binding components are known to those skilled in the art and may be selected depending on the type of assay protocol to be run. Incubation methods are also standard and are known to those skilled in the art.

In another embodiment, the term "contacting" means that the SARM compound of the present invention is introduced into a subject receiving treatment, and the SARM compound is allowed to come in contact with the androgen receptor in vivo.

As used herein, the term "treating" includes preventative as well as disorder remitative treatment. As used herein, the terms "reducing", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

The term "libido, as used herein, means sexual desire.

The term "erectile", as used herein, means capable of being erected. An erectile tissue is a tissue, which is capable of being greatly dilated and made rigid by the distension of the numerous blood vessels which it contains.

"Hypogonadism" is a condition resulting from or characterized by abnormally decreased functional activity of the gonads, with retardation of growth and sexual development. "Osteopenia" refers to decreased calcification or density of bone. This is a term which encompasses all skeletal systems in which such a condition is noted.

"Osteoporosis" refers to a thinning of the bones with reduction in bone mass due to depletion of calcium and bone protein. Osteoporosis predisposes a person to fractures, which are often slow to heal and heal poorly. Unchecked osteoporosis can lead to changes in posture, physical abnormality, and decreased mobility.

"Cognition" refers to the process of knowing, specifically the process of being aware, knowing, thinking, learning and judging. Cognition is related to the fields of psychology, linguistics, computer science, neuroscience, mathematics, ethology and philosophy. The term "mood" refers to a temper or state of the mind. As contemplated herein, alterations means any change for the positive or negative, in cognition and/or mood.

The term "depression" refers to an illness that involves the body, mood and thoughts, that affects the way a person eats, sleeps and the way one feels about oneself, and thinks about things. The signs and symptoms of depression include loss of interest in activities, loss of appetite or overeating, loss of emotional expression, an empty mood, feelings of hopelessness, pessimism, guilt or helplessness, social withdrawal, fatigue, sleep disturbances, trouble concentrating, remembering, or making decisions, restlessness, irritability, headaches, digestive disorders or chronic pain.

The term "hair loss", medically known as alopecia, refers to baldness as in the very common type of male-pattern baldness. Baldness typically begins with patch hair loss on the scalp and sometimes progresses to complete baldness and even loss of body hair. Hair loss affects both males and females.

"Anemia" refers to the condition of having less than the normal number of red blood cells or less than the normal quantity of hemoglobin in the blood. The oxygen-carrying capacity of the blood is, therefore, decreased. Persons with anemia may feel tired and fatigue easily, appear pale, develop palpitations and become usually short of breath. Anemia is caused by four basic factors: a) hemorrhage (bleeding); b) hemolysis (excessive destruction of red blood cells), c) underproduction of red blood cells; and d) not enough normal hemoglobin. There are many forms of anemia, including aplastic anemia, benzene poisoning, Fanconi anemia, hemolytic disease of the newborn, hereditary spherocytosis, iron deficiency anemia, osteoporosis, pernicious anemia, sickle cell disease, thalassemia, myelodysplastic syndrome, and a variety of bone marrow diseases. As contemplated herein, the SARM compounds of the present invention are useful in preventing and/or treating any one or more of the above-listed forms of anemia.

"Obesity" refers to the state of being well above one's normal weight. Traditionally, a person is considered to be obese if they are more than 20 percent over their ideal weight. Obesity has been more precisely defined by the National Institute of Health (NIH) as a Body to Mass Index (BMI) of 30 or above. Obesity is often multifactorial, based on both genetic and behavioral factors. Overweight due to obesity is a significant contributor to health problems. It increases the risk of developing a number of diseases including: Type 2 (adult-onset) diabetes; high blood pressure (hypertension); stroke (cerebrovascular accident or CVA); heart attack (myocardial infarction or MI); heart failure (congestive heart failure); cancer (certain forms such as cancer of the prostate and cancer of the colon and rectum); gallstones and gallbladder disease (cholecystitis); Gout and gouty arthritis; osteoarthritis (degenerative arthritis) of the knees, hips, and the lower back; sleep apnea (failure to breath normally during sleep, lowering blood oxygen); and Pickwickian syndrome (obesity, red face, underventilation and drowsiness). As contemplated herein, the term "obesity" includes any one of the above-listed obesity-related conditions and diseases. Thus the SARM compounds of the present invention are useful in preventing and/or treating obesity and any one or more of the above-listed obesity-related conditions and diseases.

"Prostate cancer" is one of the most frequently occurring cancers among men in the United States, with hundreds of thousands of new cases diagnosed each year. Over sixty percent of newly diagnosed cases of prostate cancer are found to be pathologically advanced, with no cure and a dismal prognosis. One third of all men over 50 years of age have a latent form of prostate cancer that may be activated into the life-threatening clinical prostate cancer form. The frequency of latent prostatic tumors has been shown to increase substantially with each decade of life from the 50s (5.3-14%) to the 90s (40-80%). The number of people with latent prostate cancer is the same across all cultures, ethnic groups, and races, yet the frequency of clinically aggressive cancer is markedly different. This suggests that environmental factors may play a role in activating latent prostate cancer.

In one embodiment, the SARM compounds of the present invention are administered as the sole active ingredient. However, also encompassed within the scope of the present invention are methods for hormone therapy, for treating prostate cancer, for delaying the progression of prostate cancer, and for preventing and/or treating the recurrence of prostate cancer, which comprise administering the SARM compounds in combination with one or more therapeutic agents. These agents include, but are not limited to: LHRH analogs, reversible antiandrogens, antiestrogens, anticancer drugs, 5-alpha reductase inhibitors, aromatase inhibitors, progestins, agents acting through other nuclear hormone receptors, selective estrogen receptor modulators (SERM), progesterone, estrogen, PDE5 inhibitors, apomorphine, bisphosphonate, and one or more additional SARMS, for example another SARM with AR agonistic activity.

Thus, in one embodiment, the present invention provides compositions and pharmaceutical compositions comprising a selective androgen receptor modulator compound, in combination with an LHRH analog. In another embodiment, the present invention provides compositions and pharmaceutical compositions comprising a selective androgen receptor modulator compound, in combination with a reversible anti-androgen. In another embodiment, the present invention provides compositions and pharmaceutical compositions comprising a selective androgen receptor modulator compound, in combination with an antiestrogen. In another embodiment, the present invention provides compositions and pharmaceutical compositions comprising a selective androgen receptor modulator compound, in combination with an anticancer drug. In another embodiment, the present invention provides compositions and pharmaceutical compositions comprising a selective androgen receptor modulator compound, in combination with a 5-alpha reductase inhibitor. In another embodiment, the present invention provides compositions and pharmaceutical compositions comprising a selective androgen receptor modulator compound, in combination with an aromatase inhibitor. In another embodiment, the present invention provides compositions and pharmaceutical compositions comprising a selective androgen receptor modulator compound, in combination with progesterone. In another embodiment, the present invention provides compositions and pharmaceutical compositions comprising a selective androgen receptor modulator compound, in combination with an agent acting through other nuclear hormone receptors. In another embodiment, the present invention provides compositions and pharmaceutical compositions comprising a selective androgen receptor modulator compound, in combination with a selective estrogen receptor modulators (SERM). In another embodiment, the present invention provides compositions and pharmaceutical compositions comprising a selective androgen receptor modulator compound, in combination with progesterone. In another embodiment, the present invention provides compositions and pharmaceutical compositions comprising a selective androgen receptor modulator compound, in combination with estrogen. In another embodiment, the present invention provides compositions and pharmaceutical compositions comprising a selective androgen receptor modulator compound, in combination with PDE5 inhibitors. In another embodiment, the present invention provides compositions and pharmaceutical compositions comprising a selective androgen receptor modulator compound, in combination with apomorphine. In another embodiment, the present invention provides compositions and pharmaceutical compositions comprising a selective androgen receptor modulator compound, in combination with a bisphosphonate. In another embodiment, the present invention provides compositions and pharmaceutical compositions comprising a selective androgen receptor modulator compound, in combination with one or more additional SARMS.

Pharmaceutical Compositions

The SARM compounds prepared according to the present invention may be incorporated into pharmaceutical compositions. As used herein, "pharmaceutical composition" means a "therapeutically effective amount" of the active ingredient, i.e. the SARM compound, together with a pharmaceutically acceptable carrier or diluent. A "therapeutically effective amount" as used herein refers to that amount which provides a therapeutic effect for a given condition and administration regimen.

As used herein, the term "administering" refers to bringing a subject in contact with a SARM compound of the present invention. As used herein, administration can be accomplished in vitro, i.e. in a test tube, or in vivo, i.e. in cells or tissues of living organisms, for example humans. In one embodiment, the present invention encompasses administering the compounds of the present invention to a subject.

The pharmaceutical compositions containing the SARM agent can be administered to a subject by any method known to a person skilled in the art, such as orally, parenterally, paracancerally, transmucosally, transdermally, intramuscularly, intravenously, intradermally, subcutaneously, intraperitonealy, intraventricularly, intracranially, intravaginally by inhalation or intratumorally.

In one embodiment, the pharmaceutical compositions are administered orally, and are thus formulated in a form suitable for oral administration, i.e. as a solid or a liquid preparation. Suitable solid oral formulations include tablets, capsules, pills, granules, pellets, powders, and the like. Suitable liquid oral formulations include solutions, suspensions, dispersions, emulsions, oils and the like. In one embodiment of the present invention, the SARM compounds are formulated in a capsule. In accordance with this embodiment, the compositions of the present invention comprise in addition to the SARM active compound and the inert carrier or diluent, a hard gelatin capsule.

Further, in another embodiment, the pharmaceutical compositions are administered by intravenous, intraarterial, or intramuscular injection of a liquid preparation. Suitable liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intraarterially, and are thus formulated in a form suitable for intraarterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the SARM agents or their physiologically tolerated derivatives such as salts, esters, N-oxides, and the like are prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of SARM agent over a period of time. In a further embodiment, the pharmaceutical compositions are administered intravaginally.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, cyclodextrins, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCI, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sobitan esters, stearic acids), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates), and/or adjuvants.

In one embodiment, the pharmaceutical compositions provided herein are controlled release compositions, i.e. compositions in which the SARM compound is released over a period of time after administration. Controlled or sustained release compositions include formulation in lipophilic depots (e.g. fatty acids, waxes, oils). In another embodiment, the composition is an immediate release composition, i.e. a composition in which all of the SARM compound is released immediately after administration.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321: 574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

The compositions may also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation of pharmaceutical compositions which contain an active component is well understood in the art, for example by mixing, granulating, or tablet-forming processes. The active therapeutic ingredient is often mixed with excipients which are pharmaceutically acceptable and compatible with the active ingredient. For oral administration, the SARM agents or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the SARM agents or their physiologically tolerated derivatives such as salts, esters, N-oxides, and the like are converted into a solution, suspension, or emulsion, if desired with the substances customary and suitable for this purpose, for example, solubilizers or other.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicine, the salts of the SARM will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

The following examples are presented in order to more fully illustrate the preferred embodiments of the invention. They should in no way be construed, however, as limiting the broad scope of the invention.

EXPERIMENTAL DETAILS SECTION

Example 1

Synthesis of Compound (1)

Compound (1) was synthesized as described below, and as depicted in Scheme 1.

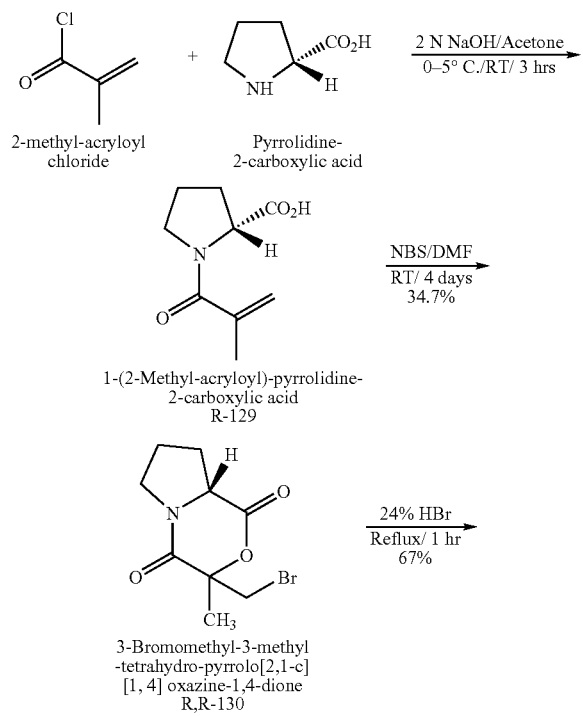

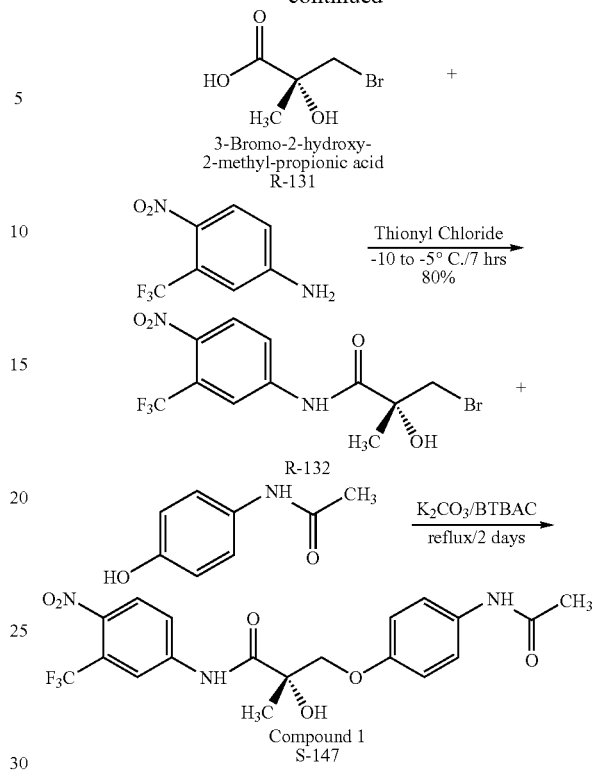

(2R)-1-Methacryloylpyrrolidin-2-carboxylic Acid (R-129). D-Proline (R-128, 14.93 g, 0.13 mol) was dissolved in 71 mL of 2 N NaOH and cooled in an ice bath; the resulting alkaline solution was diluted with acetone (71 mL). An acetone solution (71 mL) of metacrylolyl chloride 127 (13.56 g, 0.13 mol) and 2N NaOH solution (71 mL) were simultaneously added over 40 min to the aqueous solution of D-proline in an ice bath. The pH of the mixture was kept at 10-11° C. during the addition of the metacrylolyl chloride. After stirring (3 h, room temperature), the mixture was evaporated in vacuo at a temperature at 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over $Na_2SO_4$, filtered through Celite, and evaporated in vacuo to give the crude product as a colorless oil. Recrystallization of the oil from ethyl ether and hexanes afforded 16.2 (68%) of the desired compound as colorless crystals: mp 102-103° C. (lit. [214] mp 102.5-103.5° C.); the NMR spectrum of this compound demonstrated the existence of two rotamers of the title compound. $^1$H NMR (300 MHz, DMSO-$d_6$) δ 5.28 (s) and 5.15 (s) for the first rotamer, 5.15 (s) and 5.03 (s) for the second rotamer (totally 2H for both rotamers, vinyl $CH_2$), 4.48-4.44 for the first rotamer, 4.24-4.20 (m) for the second rotamer (totally 1H for both rotamers, CH at the chiral canter), 3.57-3.38 (m, 2H, $CH_2$), 2.27-2.12 (1H, CH), 1.97-1.72 (m, 6H, $CH_2$, CH, Me); $^{13}$C NMR (75 MHz, DMSO-$d_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C=O), 1647 (CO, COOH), 1584, 1508, 4459, 1369, 1348, 1178 $cm^{-1}$; $[\alpha]_D^{26}$ +80.8° (c=1, MeOH); Anal. Calcd. for $C_9H_{13}NO_3$: C, 59.00; H, 7.15; N, 7.65. Found: C, 59.13; H, 7.19; N, 7.61.

(3R,8aR)-3-Bromomethyl-3-methyl-tetrahydro-pyrrolo[2,1-c][1,4]oxazine-1,4-dione (R, R-130). A solution of NBS (23.5 g, 0.132 mol) in 100 mL of DMF was added dropwise to a stirred solution of compound R-129 (16.1 g, 88 mmol) in 70 mL of DMF under argon at room temperature, and the resulting mixture was stirred 3 days. The solvent was removed in vacuo, and a yellow solid was precipitated. The solid was suspended in water, stirred overnight at room temperature, filtered, and dried to give 18.6 (81%) (smaller weight when dried ~34%) of the title compound as a yellow solid: mp 152-154° C. (lit. [214] mp 107-109° C. for the S-isomer); $^1$H NMR (300 MHz, DMSO-d$_6$) δ 4.69 (dd, J=9.6 Hz, J=6.7 Hz, 1H, CH at the chiral center), 4.02 (d, J=11.4 Hz, 1H, CHH$_a$), 3.86 (d, J=11.4 Hz, 1H, CHH$_b$), 3.53-3.24 (m, 4H, CH$_2$), 2.30-2.20 (m, 1H, CH), 2.04-1.72 (m, 3H, CH$_2$ and CH), 1.56 (s, 2 H, Me); $^{13}$C NMR (75 MHz, DMSO-d$_6$) δ 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 cm$^{-1}$; [α]$_D^{26}$+124.5° (c=1.3, chloroform); Anal. Calcd. for C$_9$H$_{12}$BrNO$_3$: C, 41.24; H, 4.61; N, 5.34. Found: C, 41.46; H, 4.64; N, 5.32.

(2R)-3-Bromo-2-hydroxy-2-methylpropanoic Acid (R-131). A mixture of bromolactone R-130 (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated NaHCO$_3$ (100 mL×4). The aqueous solution was acidified with concentrated HCl to pH=1, which, in turn, was extracted with ethyl acetate (100 mL×4). The combined organic solution was dried over Na$_2$SO$_4$, filtered through Celite, and evaporated in vacuo to dryness. Recrystallization from toluene afforded 10.2 g (86%) of the desired compound as colorless crystals: mp 107-109° C. (lit. [214] mp 109-113° C. for the S-isomer); $^1$H NMR (300 MHz, DMSO-d$_6$) δ 3.63 (d, J=10.1 Hz, 1H, CHH$_a$), 3.52 (d, J=10.1 Hz, 1H, CHH$_b$), 1.35 (s, 3H, Me); IR (KBr) 3434 (OH), 3300-2500 (COOH), 1730 (C=O), 1449, 1421, 1380, 1292, 1193, 1085 cm$^{-1}$; [α]$_D^{26}$+10.5° (c=2.6, MeOH); Anal. Calcd. for C$_4$H$_7$BrO$_3$: C, 26.25, H, 3.86. Found: C, 26.28, H, 3.75.

N-[4-Nitro-3-(trifluoromethyl)phenyl]-(2R)-3-bromo-2-hydroxy-2-methylpropanamide (R-132). Thionyl chloride (8.6 g, 72 mmol) was added dropwise under argon to a solution of bromoacid R-131 (11.0 g, 60 mmol) in 70 mL of DMA at −5 to −10° C. The resulting mixture was stirred for 2 h under the same conditions. A solution of 4-nitro-3-trifluoromethyl-aniline (12.4 g, 60 mmol) in 80 mL of DMA was added dropwise to the above solution, and the resulting mixture was stirred overnight at room temperature. The solvent was removed on Rotavapor using high vacuum oil pump; the residue was diluted with saturated NaHCO$_3$ solution, and extracted with ethyl ether (100 mL×3). Combined extracts were dried over anhydrous Na$_2$SO$_4$, filtered through Celite, and purified by flash chromatography on silica gel, using methylene chloride as eluent to afford 18.0 g (80%) of the desired compound: mp 98-100° C. (R$_f$=0.2, silica gel, CH$_2$Cl$_2$); $^1$H NMR (300 MHz, DMSO-d$_6$) δ 10.54 (s, 1H, NH), 8.54 (d, J=2.1 Hz, 1H, ArH), 8.34 (dd, J=9.0 Hz, J=2.1 Hz, 1H, ArH), 8.18 (d, J=9.0 Hz, 1 H, ArH), 6.37 (s, 1H, OH), 3.82 (d, J=10.4 Hz, 1H, CHH$_a$), 3.58 (d, J=10.4 Hz, 1 H, CHH$_b$), 1.48 (s, 3H, Me); $^{13}$C NMR (75 MHz, DMSO-d$_6$) δ 173.6 (C=O), 143.0, 127.2, 123.2, 122.6 (q, J=33.0 Hz), 122.0 (q, J=271.5 Hz), 118.3 (q, J=6.0 Hz), 74.4, 41.4, 24.9; IR (KBr) 3344 (OH), 1680 (C=O), 1599, 1548 (C=C, Ar), 1427, 1363, 1161 cm$^{-1}$; MS (ESI): m/z 370.8 (M)$^+$; Anal. Calcd. for C$_{11}$H$_{10}$BrN$_2$O$_4$: C, 35.60, H, 2.72, N, 7.55. Found: C, 35.68, H, 2.72, N, 7.49.

N-[4-nitro-3-trifluoromethyl)phenyl]-(2S)-3-[4-(acetylamino) phenoxy]-2-hydroxy-2-methylpropanamide (S-147). The title compound was prepared from compound R-132 (0.37 g, 1.0 mmol), 4-acetamidophenol (0.23 g, 1.5 mmol) K$_2$CO$_3$ (0.28 g, 2.0 mmol), and 10% of benzyltributylammonium chloride as a phase transfer catalyst in 20 mL of methyl ethyl ketone was heated at reflux overnight under argon. The reaction was followed by TLC, the resulting mixture was filtered through Celite, and concentrated in vacuo to dryness. Purification by flash column chromatography on silica gel (hexanes-ethyl acetate, 3:1) yielded 0.38 g (86%) (R$_f$=0.18 hexanes-ethyl acetate, 3:1) of the desired compound as a light yellow powder: mp 70-74° C.; The solid can be recrystalized from ethyl acetate and hexane); $^1$H NMR (300 MHz, DMSO-d$_6$) δ 10.62 (s, 1H, NH), 9.75 (s, 1H, NH), 8.56 (d, J=1.9 Hz, 1H, ArH), 8.36 (dd, J=9.1 Hz, J=1.9 Hz, 1H, ArH), 8.18 (d, J=9.1 Hz, 1H, ArH), 7.45-7.42 (m, 2H, ArH), 6.85-6.82 (m, 2H, ArH), 6.25 (s, 1H, OH), 4.17 (d, J=9.5 Hz, 1 H, CHH$_a$), 3.94 (d, J=9.5 Hz, 1H, CHH$_b$), 1.98 (s, 3H, Me), 1.43 (s, 3H, Me); $^{13}$C NMR (75 MHz, DMSO-d$_6$) δ 174.6 (C=O), 167.7, 154.2, 143.3, 141.6, 132.8, 127.4, 123.0, 122.7 (q, J=33.0 Hz), 122.1 (q, J=271.5 Hz), 120.1, 118.3 (q, J=6.0 Hz), 114.6, 74.9, 73.8, 23.8, 23.0; IR (KBr) 3364 (OH), 1668 (C=O), 1599, 1512 (C=C, Ar), 1457, 1415, 1351, 1323, 1239, 1150 1046 cm$^{-1}$; MS (ESI): m/z 464.1 (M+Na)$^+$; Anal. Calcd. for C$_{19}$H$_{18}$F$_3$N$_3$O$_6$: C, 51.71; H, 4.11; N, 9.52. Found: C, 52.33; H, 4.40; N, 9.01.

The synthesis of the various ether analogs of compound (1) utilizes the common intermediate that is the final reaction step. Bromo-intermediates are used which allow various phenolic compounds to displace the bromide to give the desired ether product. Bromohydrin was converted to an epoxide and to open the epoxide to give the same desired ether product.

Melting points were determined on a Thomas-Hoover capillary melting point apparatus and are uncorrected. Infrared spectra were recorded on a Perkin Elmer System 2000 FT-IR. Optical rotations were determined on an Autopol® III Automatic Polarimeter (Rudolph Research Model III-589-10, Fairfield, N.J.). Proton and carbon-13 magnetic resonance spectra were obtained on a Bruker AX 300 spectrometer (300 and 75 MHz for $^1$H and $^{13}$C, respectively). Chemical shift values were reported as parts per million (δ) relative to tetramethylsilane (TMS). Spectral data were consistent with assigned structures. Mass spectra were determined on a Bruker-HP Esquire LC System. Elemental analyses were performed by Atlantic Microlab Inc. (Norcross, Ga.), and found values were within 0.4% of the theoretical values. Routine thin-layer chromatography (TLC) was performed on silica gel on aluminum plates (silica gel 60 F 254, 20×20 cm, Aldrich Chemical Company Inc., Milwaukee, Wis.). Flash chromatography was performed on silica gel (Merck, grade 60, 230-400 mesh, 60). Tetrahydrofuran (THF) was dried by distillation over sodium metal. Acetonitrile (MeCN) and methylene chloride (CH$_2$Cl$_2$) were dried by distillation from P$_2$O$_5$.

Example 2

Large Scale Syntheiss of Compound (1)

Compound (1) (3-[4-(acetylamino)phenoxy]-2-Hydroxy-2-methyl-N-[3trifluoro methyl-4-nitro-phenyl)-propriona-mide) is a member of the oxolutamide family of androgen receptor agonists, and is a nonsteroidal selective androgen receptor modulator (SARM). It binds the androgen receptor in vitro with high affinity (Ki=7.5±0.5 nM). In vivo it acts as a partial agonist at the androgen receptor and results in strong anabolic and weakly androgenic effects. Compound (1) has no other known endocrine activities.

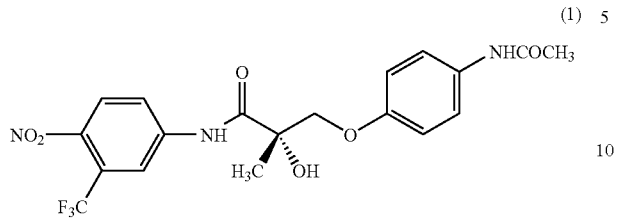

(1)

Compound (2) was synthesized according to the following synthetic Steps:

Step 1—Synthesis of (2R)-1-Methacryloylpyrrolidin-2-carboxylic acid (R-129)

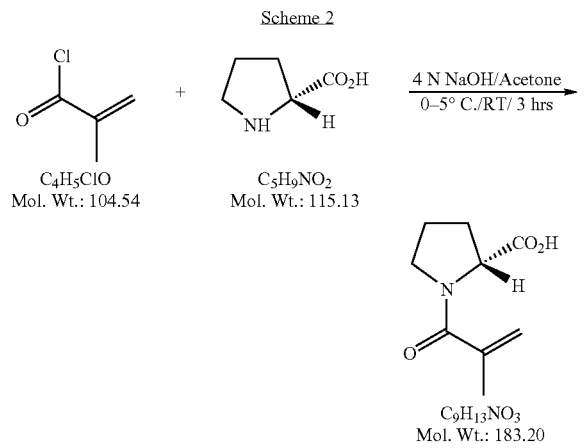

Scheme 2

A 72 L flask with a mechanical stirrer and inlet for inert atmosphere was set up in a cooling bath. The flask was placed under argon and charged with 5000 g (43.4 moles) of D-proline [ICN lot# 7150E, ≧99%], 11.9 L of 4N NaOH, and 12 L acetone. The mixture was cooled to 5° C. on an ice bath. A solution of 4548.8 g (43.5 moles) of methacryloyl chloride [Aldrich lot#12706HO, 98+%] in 12.0 L of acetone was prepared. The solution of methacryloyl chloride and 11.9 L of 4N NaOH were added simultaneously to the reaction mixture in the 72 L flask. During the addition, the temperature was maintained less than 10° C. and the pH of the reaction mixture was maintained at greater than or equal to 10. The pH was maintained by adding the 4N NaOH more slowly or more quickly depending on the pH of the solution. The addition time was approximately 2 hours and 40 minutes. After the addition was complete, the reaction mixture was stirred overnight and allowed to warm to room temperature.

The acetone was removed on a rotary evaporator, and the aqueous mixture was extracted with t-butyl methyl ether (28.0 L). The mixture was then acidified with concentrated HCl (6568.1 g) to a pH of less than 2. The product was isolated by extraction into methylene chloride (3×20 L). The extracts were concentrated on a rotary evaporator. T-Butyl methyl ether (10 L) was added and concentrated on the rotary evaporator to perform a solvent exchange. Additional t-Butyl methyl ether (10 L) was added to precipitate the product. Ice was charged to the rotary evaporator bath and the product was allowed to crystallize. The crystalline product was collected and isolated by filtration. The weight after drying in a vacuum oven at 50° C. was 4422.2 g (55.6% yield).

Step 2-Synthesis of (3R,8R)-3-Bromomethyl-3-methyl-tetrahydropyrolo[2,1-c][1,4]oxazine-1,4-dione (R,R-130)

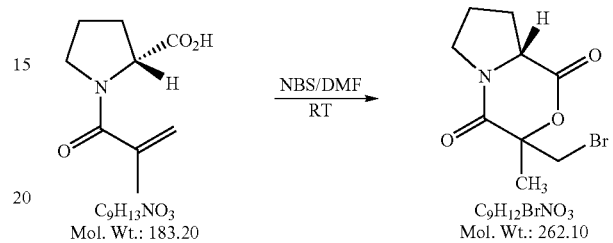

Scheme 3

A 50 L flask was set up with a mechanical stirrer, inlet for inert atmosphere, and cooling capacity. The flask was placed under an argon atmosphere and was charged with 4410.0 g (24.1 moles) of R-129 and 8.8 L of DMF. Then NBS (6409.6 g, 36.0 moles) was added slowly over a period of 2 hours and 7 minutes. The reaction mixture was agitated for at least 8 hours. Water (20.0 L) was added to precipitate the product. The product was allowed to stir for at least 4 hours to crystallize. The crystalline product was collected and isolated by filtration. The weight after drying in a vacuum oven at 50° C. was 5532.1 g (87.7% yield).

Step 3-Synthesis of (2R)-3-Bromo-2-hydroxy-2-methylpropanoic acid (R-131)

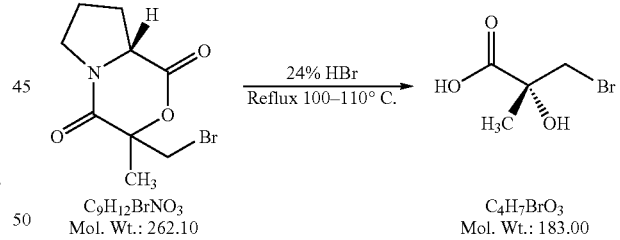

Scheme 4

A 50 L flask was set up with a mechanical stirrer, inlet for inert atmosphere, and heating capacity. The flask was placed under an argon atmosphere and was charged with 5472.3 g (20.8 moles) of R,R-130 and 14.175 L of deionized water and 14,118.4 g of 48% HBr. The reaction mixture was heated to 102° C. for 6 hours, and allowed to cool 31° C. Brine (20 L) was added to the reaction mixture and the product was extracted with 6×20.4 L of t-butyl methyl ether. The organic layers were combined and concentrated with the rotary evaporator. Toluene (4.0 L) was charged to the rotary evaporator. The product was dried by toluene distillation. The mixture was concentrated with the rotary evaporator. The product was recrystallized from toluene (45.0 L) by heating to 100° C. to dissolve the product. The flask was cooled on ice and the product was allowed to crystallize. The crystalline product was collected by filtration and washed with toluene (3.4 L). The weight after drying in a vacuum oven at 50° C. was 3107.0 g (81.3% yield).

Step 4—Synthesis of N-[4-Nitro-3-(trifluoromethyl) phenyl]-(2R)-3-bromo-2-hydroxy-2-methylpropanamide (R-132)

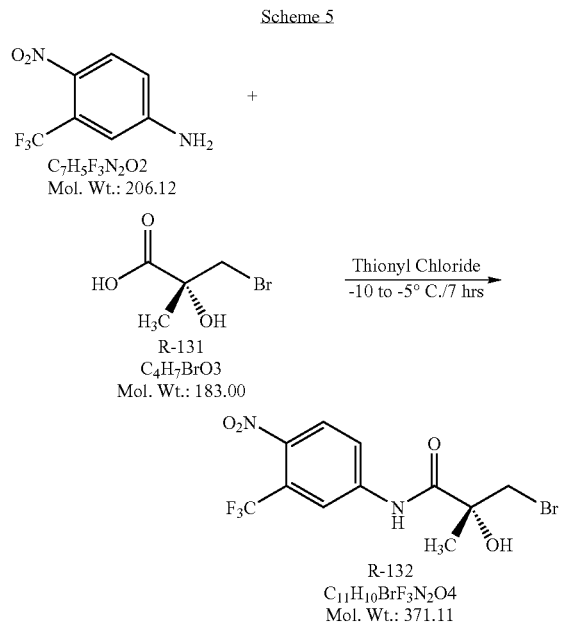

A 50 L flask was set up with a mechanical stirrer, inlet for inert atmosphere, and cooling capacity. The flask was placed under an argon atmosphere and was charged with 2961.5 g (16.2 moles) of R-131 and 9.0 L of THF. The flask was cooled on ice to less than 5° C. Thionyl chloride (1200 mL, 16.4 moles) dissolved in 6.0 L of THF was added slowly via an addition funnel to the reaction flask. The temperature of the reaction flask was maintained less than or equal to 10° C. The addition time was 1 hour 10 minutes. The reaction mixture was allowed to agitate for an additional 2 hours 50 minutes. Then a solution of 2359.4 g of (11.4 moles) of 4-nitro-3-trifluoromethylaniline (Aldrich, 98%) and 3.83 L of triethylamine in 6.0 L THF was added over a period of 3 hours 5 minutes. The temperature of the reaction flask was maintained less than or equal to 10° C. The ice bath was removed, and the reaction mixture was allowed to stir for 30 minutes. With a heating mantle, the reaction mixture was heated to 50° C. for 15 hours and 10 minutes. After the reaction was complete as analyzed by TLC, the reaction mixture was cooled to less than 30° C. and 7.5 L of deionized water was added. The aqueous layer was removed and a second water wash (7.5 L) was performed. The organic layer was then washed three times with 10% bicarbonate (8.1 L) until the pH was greater than 7.

The solvent was removed on a rotary evaporator. Toluene (3.0 L) was added and then removed on the rotary evaporator to dry the crude product. The product was dissolved in 2.0 L of toluene at 65° C. Upon cooling the product crystallized. The crystalline product was collected and isolated by filtration. The wet cake was washed with 1.0 L of toluene. The weight after drying in a vacuum oven at 50° C. was 3751.0 g (70.3% yield).

Step 5—Synthesis of Compound 1

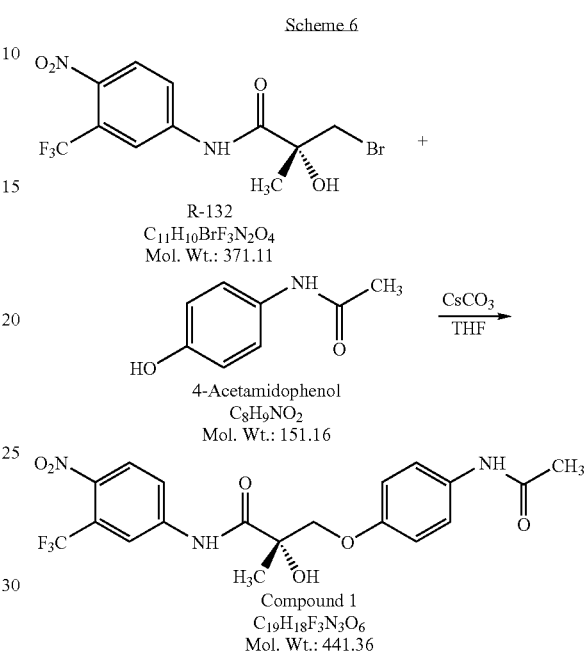

A 22 L flask was set up with a mechanical stirrer, inlet for inert atmosphere, and cooling capacity. The flask was placed under an argon atmosphere and was charged with 1002.8 g (2.70 moles) of R-132, 4.0 L of THF, and 454.2 g (3.00 moles) of 4-acetamidophenol (Aldrich, 98%). While stirring, the flask was then charged with 1769.9 g of cesium carbonate (Aldrich, 99%). The flask was heated to reflux for at least 8 hours, and the reaction monitored by TLC [silica gel, dichloromethane/hexane 3:1, Epoxide Rf=0.5]. When the reaction was complete, the flask was allowed to cool to room temperature.

Water was added to dissolve the carbonate and ethyl acetate was added to help with the phase separations. The aqueous phase was separated as waste. The organic phase was washed with a second portion of water. The organic layer was transferred to a rotary evaporator and the solvent was removed. The solvent was exchanged into ethanol by charging ethanol into the rotovap flask and removing some of the ethanol to remove all of the ethyl acetate. The ethanol solution was added to water to precipitate the product. The crude product was collected by filtration and washed with water. The product was transferred back to the rotary evaporator for crystallization. Ethyl acetate was charged to the rotovap flask to exchange the solvent into ethyl acetate. The ethyl acetate was removed under vacuum which dried the product. A minimum amount of ethyl acetate was added to dissolve the product at 60° C. t-Butyl methyl ether was added to crystallize the product. After cooling, the product was collected by filtration and washed with t-Butyl methyl ether. The wet cake was added back to the rotary evaporator and ethanol was charged. A solvent exchange into ethanol, removed the residual t-Butyl methyl ether. Filtering the ethanol solution into water recrystallized the product. After stirring, the product was collected by filtration and washed with water. The weight after drying in a vacuum oven oat 50° C. was 52%.

The process described herein in Example 2 provides an improvement over previous methods (such as the methods described in Example 2 hereinabove) Specifically, the improvements in Step 1 include the use of t-butyl methyl to extract the product instead of ethyl acetate. In addition, the product is crystallized from t-butyl methyl ester instead of diethyl ether. The improvements in Step 2 include reducing the amount of DMF. Further, the addition of water to DMF precipitates the product which can then be collected by filtration. The improvements in Step 3 include reducing the amount of water in the reaction, and crystallization of the product from toluene. In addition, t-butylmethyl ether is used for the extraction, as this improves the phase separation. The improvements in Step 4 include the use of toluene to recrystallize the product. In addition, THF is used as a solvent. Finally, the improvements in Step 5 include the use of ethanol/water for the purification of the final SARM compound.

Example 3

Large Scale Synthesis of Compound (2)

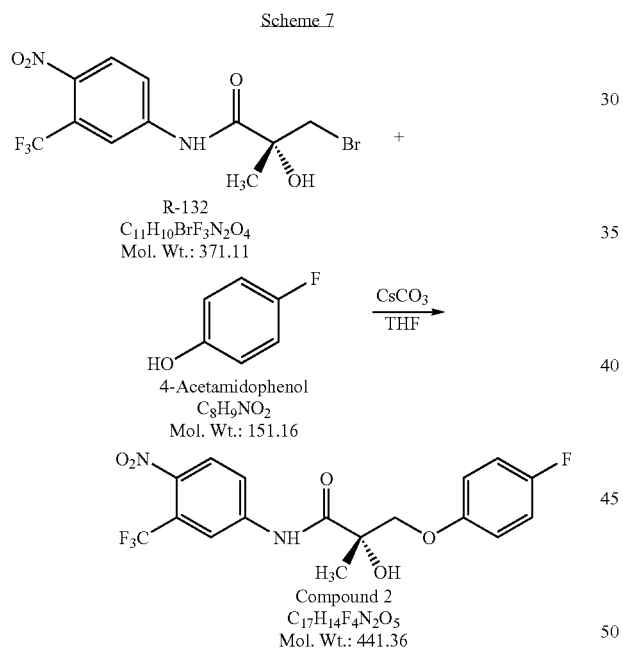

A 12 L flask was set up with a triblade propeller style mechanical stirrer, inlet for inert atmosphere, and cooling bath. The flask was placed under an argon atmosphere and was charged with 1250 g (3.37 moles) of R-132 and 5.0 L of anhydrous THF. 416.8 g (3.71 moles) of 4-fluorophenol and 2008.9 g (6.17 moles) of cesium carbonate were charged to the reaction flask. The reaction mixture was heated to 50° C. with vigorous mixing. The reaction was monitored HPLC. The reaction was complete when the HPLC showed that the starting material (R-132) was less than 5% after 3 hours at 50° C. The reaction mixture was filtered and the wet cake washed with THF (2.5 L). The product was concentrated on a rotary evaporator. 2.5 L of ethanol was charged to the rotary evaporator and the solvent was removed to remove all the THF. 6.25 L of ethanol was used to transfer the material in the rotary evaporator to a 22 L flask. Deionized water (12 L) was slowly charged to the flask to precipitate the product. The mixture was stirred for 16 hours and filtered to collect the bright yellow product. The wet cake was washed with water (2.5 L). The wet cake was charged to the rotary evaporator and 6.25 L of ethanol was charged and warmed to dissolve the product. The solution was filtered through a 0.2 micron filter into a clean 22 liter flask. Deionized water (6.25 L) was slowly filtered through the 0.2 micron filter to the flask to precipitate the product. The mixture was stirred for 17 hours and filtered to collect the product. The wet cake was washed with water (1.25 L). The wet cake was charged back to the flask and 6.25 L of deionized water was filtered through the 0.2 micron filter into the flask. The mixture was stirred for 23 hours and filtered to collect the product. The product was dried in a vacuum oven at 25° C. The yield was 1128 g (83% yield).

It will be appreciated by a person skilled in the art that the present invention is not limited by what has been particularly shown and described hereinabove. Rather, the scope of the invention is defined by the claims that follow:

What is claimed is:
1. A process for preparing a selective androgen receptor modulator (SARM) compound represented by the structure of formula 1:

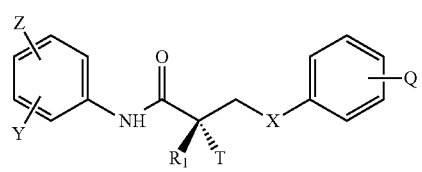

wherein
X is O;
T is OH, OR, NHCOCH$_3$, or NHCOR;
Z is NO$_2$, CN, COOH, COR, NHCOR or CONHR;
Y is CF$_3$, F, I, Br, Cl, CN, C(R)$_3$ or Sn(R)$_3$;
Q is alkyl, halogen, CF$_3$, CN C(R)$_3$, Sn(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR; or Q together with the benzene ring to which it is attached is a fused ring system represented by structure A, B or C:

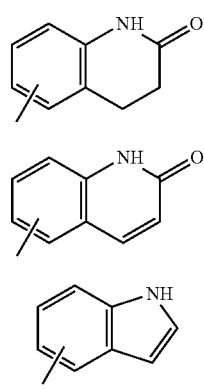

R is alkyl, haloalkyl, dihaloalkyl, trihaloalkyl, CH$_2$F, CHF$_2$, CF$_3$, CF$_2$CF$_3$, aryl, phenyl, halogen, alkenyl or OH; and R$_1$ is CH$_3$, CH$_2$F, CHF$_2$, CF$_3$, CH$_2$CH$_3$, or CF$_2$CF$_3$;

said process comprising the steps of:

coupling an amide of formula II:

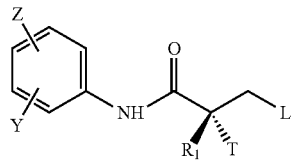

wherein Z, Y, R$_1$ and T are as defined above and L is a leaving group, with a compound of formula III:

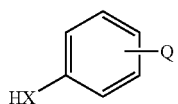

wherein Q and X are as defined above, producing said compound of formula I; and a purification step consisting of precipitating said compound of formula (1) in a mixture of alcohol and water alone.

2. The process according to claim 1, wherein said alcohol is ethanol.

3. The process according to claim 1, further comprising the step of collecting said crystallized compound by filtration.

4. The process according to claim 1, wherein T is OH.

5. The process according to claim 1, wherein R$_1$ is CH$_3$.

6. The process according to claim 1, wherein Z is NO$_2$.

7. The process according to claim 1, wherein Z is CN.

8. The process according to claim 1, wherein Y is CF$_3$.

9. The process according to claim 1, wherein Q is NHCOCH$_3$.

10. The process according to claim 1, wherein Q is F.

11. The process according to claim 1, wherein Q is in the para position.

12. The process according to claim 1, wherein Z is in the para position.

13. The process according to claim 1, wherein Y is in the meta position.

14. The process according to claim 1, wherein said SARM compound is represented by the structure of formula (IV):

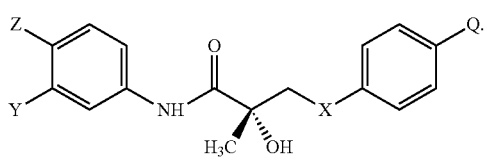

15. The process according to claim 1, wherein said SARM compound is represented by the structure of formula (1):

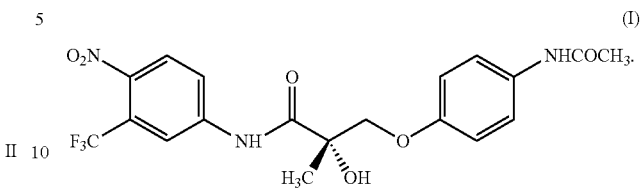

16. The process according to claim 1, wherein said SARM compound is represented by the structure of formula (2):

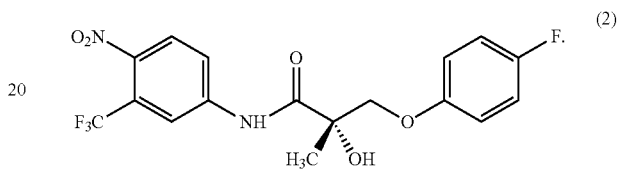

17. The process according to claim 1, wherein said SARM compound is represented by the structure of formula (3):

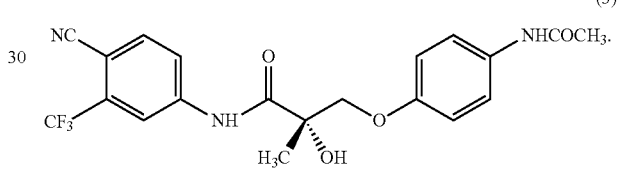

18. The process according to claim 1, wherein said SARM compound is represented by the structure of formula (4):

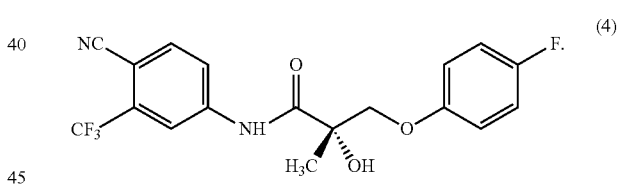

19. The process according to claim 1, wherein said coupling step is carried out in the presence of a base.

20. The process according to claim 1, wherein the leaving group L is Br.

21. The process according to claim 1, wherein the amide of formula II is prepared by
a) converting a cyclic compound of formula IX wherein L and R$_1$ are as defined above and T$_1$ is O or NH, to a compound of formula VIII wherein L and R$_1$ are as defined above and T$_2$ is OH or NH$_2$;

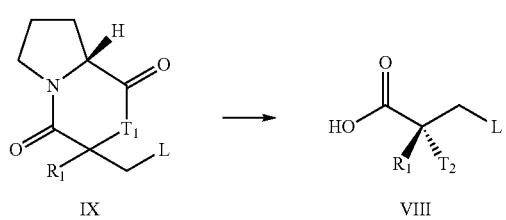

b) reacting an amine of formula VII:

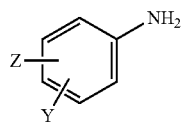

wherein Z and Y are as defined above, with the carboxylic acid of formula VIII in the presence of a coupling reagent, to produce an amide of formula IIA; and

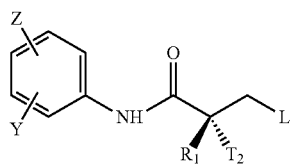

c) optionally converting $T_2$ to T, as defined above.

22. The process according to claim 21, wherein step (a) is carried out in the presence of HBr.

23. The process according to claim 1, further comprising the step of converting said selective androgen receptor modulator (SARM) compound to its optical isomer, pharmaceutically acceptable salt, N-oxide, or any combination thereof.

24. The process according to claim 1, wherein the SARM compound has in-vivo androgenic and anabolic activity of a nonsteroidal ligand for the androgen receptor.

25. A process for preparing a selective androgen receptor modulator (SARM) compound represented by the structure of formula I:

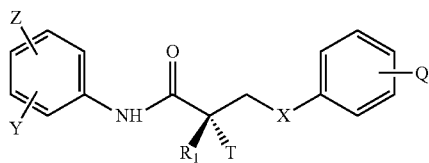

wherein
X is O,
T is OH, OR, NHCOCH$_3$, or NHCOR;
Z is NO$_2$, CN, COOH, COR, NHCOR or CONHR;
Y is CF$_3$, F, I, Br, Cl, CN, C(R)$_3$ or Sn(R)$_3$;
Q is alkyl, halogen, CF$_3$, CN, C(R)$_3$, Sn(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR; or Q together with the benzene ring to which it is attached is a fused ring system resented by structure A, B or C:

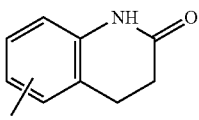

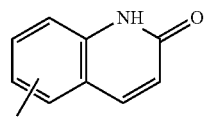

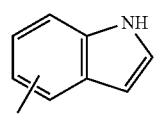

R is alkyl, haloalkyl, dihaloalkyl, trihaloalkyl, CH$_2$F, CHF$_2$, CF$_3$, CF$_2$CF$_3$, aryl, phenyl, halogen, alkenyl or OH; and
R$_1$ is CH$_3$, CH$_2$F, CHF$_2$, CF$_3$, CH$_2$CH$_3$, or CF$_2$CF$_3$;
said process comprising the steps of:
coupling an amide of formula II:

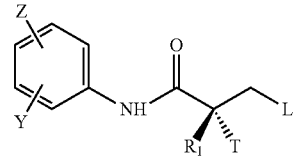

wherein Z, Y, R$_1$ and T are as defined above and L is a leaving group,
with a compound of formula III:

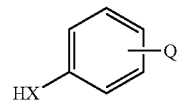

wherein Q and X are as defined above, producing said compound of formula I; and a purification step consisting of precipitating said compound of formula (I) in a mixture of ethanol and water alone.

26. The process according to claim 25, further comprising the step of collecting said crystallized compound by filtration.

27. The process according to claim 25, wherein T is OH.

28. The process according to claim 25, wherein R$_1$ is CH$_3$.

29. The process according to claim 25, wherein Z is NO$_2$.

30. The process according to claim 25, wherein Z is CN.

31. The process according to claim 25, wherein Y is CF$_3$.

32. The process according to claim 25, wherein Q is NHCOCH$_3$.

33. The process according to claim 25, wherein Q is F.

34. The process according to claim 25, wherein Q is in the para position.

35. The process according to claim 25, wherein Z is in the para position.

36. The process according to claim 25, wherein Y is in the meta position.

37. The process according to claim 25, wherein said SARM compound is represented by the structure of formula (IV):

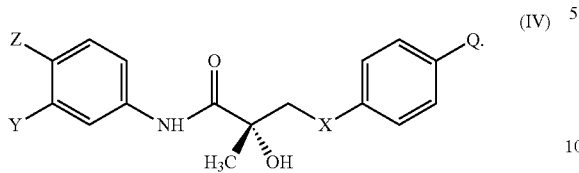

38. The process according to claim 25, wherein said SARM compound is represented by the structure of formula (1):

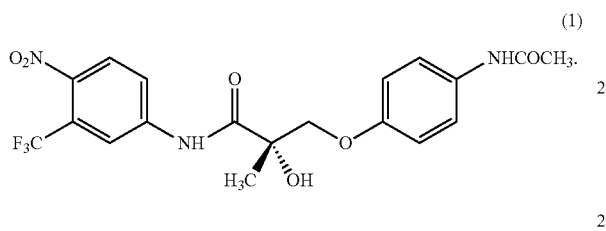

39. The process according to claim 25, wherein said SARM compound is represented by the structure of formula (2):

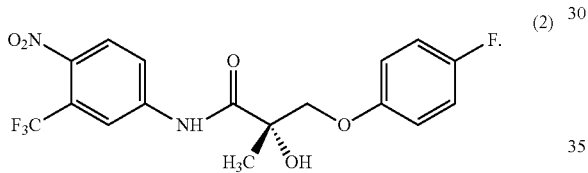

40. The process according to claim 25, wherein said SARM compound is represented by the structure of formula (3):

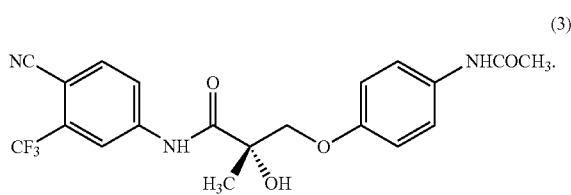

41. The process according to claim 25, wherein said SARM compound is represented by the structure of formula (4):

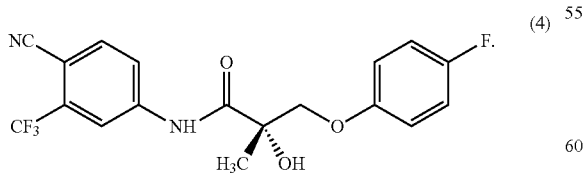

42. The process according to claim 25, wherein said coupling step is carried out in the presence of a base.

43. The process according to claim 25, wherein the leaving group L is Br.

44. The process according to claim 25, wherein the amide of formula II is prepared by
  d) converting a cyclic compound of formula IX wherein L and $R_1$ are as defined above and $T_1$ is O or NH, to a compound of formula VIII wherein L and $R_1$ are as defined above and $T_2$ is OH or $NH_2$;

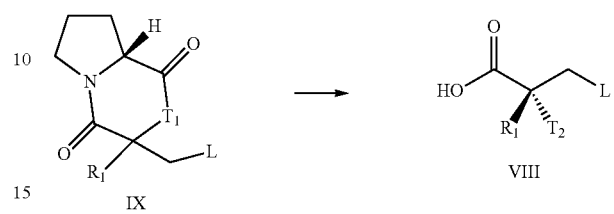

e) reacting an amine of formula VII:

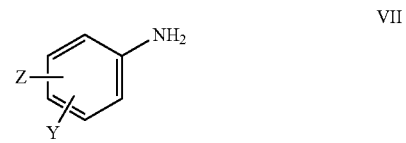

wherein Z and Y are as defined above, with the carboxylic acid of formula VIII in the presence of a coupling reagent, to produce an amide of formula IIA; and

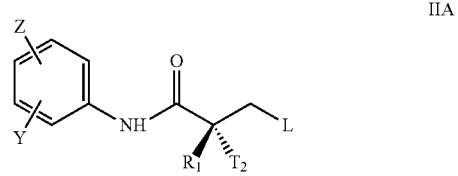

f) optionally converting $T_2$ to T.

45. The process according to claim 44, wherein step (a) is carried out in the presence of HBr.

46. The process according to claim 25, further comprising the step of converting said selective androgen receptor modulator (SARM) compound to its pharmaceutically acceptable salt, N-oxide, or any combination thereof.

47. The process according to claim 25, wherein the SARM compound has in-vivo androgenic and anabolic activity of a nonsteroidal ligand for the androgen receptor.

48. A process for preparing a selective androgen receptor modulator (SARM) compound represented by the structure of formula I:

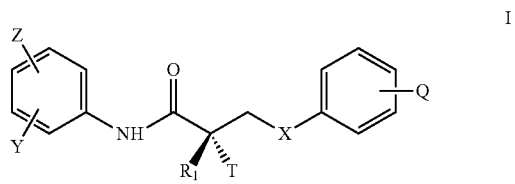

wherein
X is O;
T is OH, OR, $NHCOCH_3$, or NHCOR;
Z is $NO_2$, CN, COOH, COR, NHCOR or CONHR;
Y is $CF_3$, F, I, Br, Cl, CN, $C(R)_3$ or $Sn(R)_3$;

Q is alkyl, halogen, $CF_3$, CN, $C(R)_3$, $Sn(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR; or Q together with the benzene ring to which it is attached is a fused ring system represented by structure A, B or C:

A

B

C

R is alkyl, haloalkyl, dihaloalkyl, trihaloalkyl, $CH_2F$, $CHF_2$, $CF_3$, $CF_2CF_3$, aryl, phenyl, halogen, alkenyl or OH; and $R_1$ is $CH_3$, $CH_2F$, $CHF_2$, $CF_3$, $CH_2CH_3$, or $CF_2CF_3$;

said process comprising the steps of:

a) converting a cyclic compound of formula IX wherein $R_1$ is as defined above, L is a leaving group, and $T_1$ is O or NH, to a compound of formula VIII wherein L and $R_1$ are as defined above and $T_2$ is OH or $NH_2$;

IX → VIII b) reacting an amine or formula VII:

VII wherein Z and Y are as defined above, with the carboxylic acid of formula VIII in the presence of a coupling reagent, to produce an amide of formula IIA;

IIA c) optionally converting $T_2$ to T to generate a compound of formula II;

II d) coupling the amide of formula II with a compound of formula III;

III wherein Q and X are as said compound of formula I and a purification step consisting of precipitating said compound of formula (I) in a mixture of alcohol and water alone.

49. The process according to claim 48, further comprising the step of collecting said crystallized compound by filtration.

50. The process according to claim 48, wherein T is OH.

51. The process according to claim 48, wherein $R_1$ is $CH_3$.

52. The process according to claim 48, wherein Z is $NO_2$.

53. The process according to claim 48, wherein Z is CN.

54. The process according to claim 48, wherein Y is $CF_3$.

55. The process according to claim 48, wherein Q is $NHCOCH_3$.

56. The process according to claim 48, wherein Q is F.

57. The process according to claim 48, wherein Q is in the para position.

58. The process according to claim 48, wherein Z is in the para position.

59. The process according to claim 48, wherein Y is in the meta position.

60. The process according to claim 48, wherein said SARM compound is represented by the structure of formula (IV):

(IV)

61. The process according to claim 48, wherein said SARM compound is represented by the structure of formula (1):

(1)

62. The process according to claim 48, wherein said SARM compound is represented by the structure of formula (2):

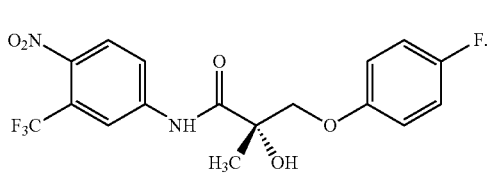

(2)

63. The process according to claim 48, wherein said SARM compound is represented by the structure of formula (3):

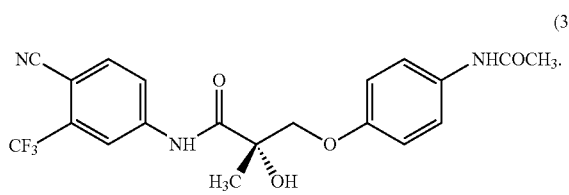

(3)

64. The process according to claim 48, wherein said SARM compound is represented by the structure of formula (4):

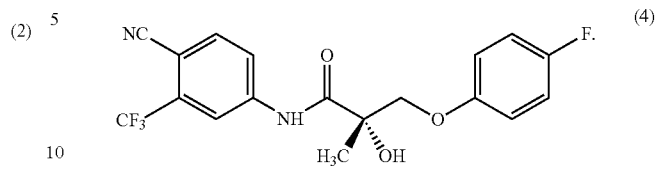

(4)

65. The process according to claim 48, wherein said coupling step is carried out in the presence of a base.

66. The process according to claim 48, wherein the leaving group L is Br.

67. The process according to claim 48, wherein step (a) is carried out in the presence of HBr.

68. The process according to claim 48, further comprising the step of converting said selective androgen receptor modulator (SARM) compound to its pharmaceutically acceptable salt, N-oxide, or any combination thereof.

69. The process according to claim 48, wherein the SARM compound has in-vivo androgenic and anabolic activity of a nonsteroidal ligand for the androgen receptor.

* * * * *